(12) United States Patent
Sano

(10) Patent No.: US 8,881,417 B2
(45) Date of Patent: Nov. 11, 2014

(54) ANGLE MEASURING DEVICE

(75) Inventor: Koji Sano, Tokyo (JP)

(73) Assignee: Yuki Trading Co., Ltd., Tokyo (JP)

( * ) Notice: Subject to any disclaimer, the term of this patent is extended or adjusted under 35 U.S.C. 154(b) by 0 days.

(21) Appl. No.: 14/236,198

(22) PCT Filed: Jul. 2, 2012

(86) PCT No.: PCT/JP2012/066918
§ 371 (c)(1),
(2), (4) Date: Jan. 30, 2014

(87) PCT Pub. No.: WO2014/006683
PCT Pub. Date: Jan. 9, 2014

(65) Prior Publication Data
US 2014/0190030 A1    Jul. 10, 2014

(51) Int. Cl.
*A61B 5/107*    (2006.01)
*G01B 5/24*    (2006.01)

(52) U.S. Cl.
CPC ............... *A61B 5/1071* (2013.01); *A61B 5/107* (2013.01); *G01B 5/24* (2013.01)
USPC .................................. 33/512; 33/806; 33/783

(58) Field of Classification Search
CPC ...... G01B 5/24; A61B 5/1071; A61B 5/1072; A61B 5/1076; A61B 5/107
USPC .................. 33/512, 806–810, 783, 784, 795, 33/501.05, 501.06, 501.08
See application file for complete search history.

(56) References Cited

U.S. PATENT DOCUMENTS

| | | | | |
|---|---|---|---|---|
| 1,829,323 A | * | 10/1931 | Witter et al. | 33/824 |
| 1,863,236 A | | 6/1932 | Brienza | |
| 2,767,893 A | * | 10/1956 | Latson | 269/43 |
| 3,300,864 A | * | 1/1967 | Lesslie | 33/512 |

(Continued)

FOREIGN PATENT DOCUMENTS

| | | |
|---|---|---|
| JP | 6-7325 A | 1/1994 |
| JP | 2008-295527 A | 12/2008 |
| JP | 2009-204325 A | 9/2009 |
| JP | 4445468 B2 | 1/2010 |

OTHER PUBLICATIONS

International Search Report issued in PCT/JP2012/066918 with English Translation having a mailing date of Aug. 28, 2012 (6 pages).

*Primary Examiner* — Yaritza Guadalupe-McCall
(74) *Attorney, Agent, or Firm* — Flynn, Thiel, Boutell & Tanis, P.C.

(57) ABSTRACT

An angle measuring device 2 is configured to detect an angle formed between a measured line LX connecting a first position PL and a second position PR and a predetermined reference plane. The angle measuring device 2 includes: a case 10; a first pointing mechanism 30L for pointing the first position PL; a second pointing mechanism 30R for pointing the second position PR; moving mechanisms 60L and 60R that allow at least one of the first and second pointing mechanisms 30L and 30R to be movable; and a turning member angular scale mark 72 that indicates a moved amount of at least one of the first and second pointing mechanisms 30L and 30R by the moving mechanisms 60L and 60R. The moving mechanisms 60L and 60R move the first pointing mechanism 30L and the like so that a line segment connecting the first pointing mechanism 30L and the second pointing mechanism 30R includes the measurement reference plane or becomes parallel to the measurement reference plane.

16 Claims, 24 Drawing Sheets

(56) References Cited

U.S. PATENT DOCUMENTS

| | | | |
|---|---|---|---|
| 3,745,661 A * | 7/1973 | Atzberger | 33/795 |
| 4,846,194 A | 7/1989 | Sabia | |
| 4,872,268 A | 10/1989 | Perrault | |
| 5,174,030 A * | 12/1992 | Clot et al. | 33/3 C |
| 5,249,366 A * | 10/1993 | Takahashi et al. | 33/811 |
| 5,966,827 A * | 10/1999 | Horvath et al. | 33/512 |
| 6,205,672 B1 * | 3/2001 | Paulsen et al. | 33/784 |
| 6,301,799 B1 * | 10/2001 | Ho | 33/807 |
| 6,508,012 B2 * | 1/2003 | Wells, Jr. | 33/784 |
| 6,565,519 B2 | 5/2003 | Benesh | |
| 6,990,746 B2 * | 1/2006 | Penna et al. | 33/784 |
| 7,246,450 B1 * | 7/2007 | Mason | 33/784 |
| 7,275,335 B2 * | 10/2007 | Holec et al. | 33/784 |
| 7,328,520 B2 * | 2/2008 | Galle, Sr. | 33/783 |
| 7,347,002 B2 * | 3/2008 | Foege | 33/783 |
| 8,024,869 B2 * | 9/2011 | Duarte | 33/784 |
| 8,201,342 B2 * | 6/2012 | Gerster | 33/512 |
| 2002/0083613 A1 * | 7/2002 | Wells, Jr. | 33/784 |
| 2003/0051361 A1 * | 3/2003 | Economaki | 33/534 |
| 2006/0283037 A1 * | 12/2006 | Galle | 33/783 |
| 2007/0039197 A1 * | 2/2007 | Holec et al. | 33/784 |
| 2007/0089315 A1 * | 4/2007 | Foege | 33/783 |
| 2008/0189971 A1 * | 8/2008 | Wo | 33/784 |
| 2012/0159798 A1 * | 6/2012 | Kozykowski | 33/534 |
| 2013/0152419 A1 * | 6/2013 | Stockman | 33/701 |

* cited by examiner

ANGLE MEASURING DEVICE

FIELD

The present invention relates to an angle measuring device.

BACKGROUND

There has been known an angle measuring device for measuring an angle formed between a measured line and a vertical line. For example, in the field of rehabilitation, the angle measuring device described in Japanese Patent No. 4445468, for example, is used when measuring angles at various positions of a body. Such an angle measuring device includes: a first arm; a second arm; a support member attached to one end of the second arm; angular scale marks indicating opening angles of the first and second arms; and an inclination angle meter that detects an orientation of the support member with respect to the vertical line.

SUMMARY

Technical Problem

In a case where the above-described angle measuring device is used, however, work load on a measurer is tremendous since the measurer needs to perform all of measurement work while looking at scale marks of the inclination angle meter and work of recording the measured angle. Furthermore, the number of measured positions on one measured person is generally not small such as one or two but many. Thus, an amount of time required for the measurements becomes long. Thus, the prolonged measurement time places a heavy burden on the measurer or the measured person. In a case where the measured person is undergoing rehabilitation, in particular, the magnitude of the burden on that measured person is immeasurable.

Given this situation, an angle measuring device capable of measuring an angle easily is in demand.

The present invention has been made in view of the above-described problem, and an object thereof is to provide an angle measuring device capable of simplifying angle measurement work.

Solution to Problem

Owing to the earnest investigation made by the present inventor, the above-described object is achieved by the following means.

An angle measuring device, for measuring an angle formed between a measured line connecting a first position and a second position on a body and a predetermined reference line by using a sensor capable of detecting the angle, includes: a first pointing device for pointing the first position; a second pointing device for pointing the second position; a holding device for holding the first pointing device or the second pointing device; a moving mechanism that allows the holding device to be movable so that a line segment connecting the first pointing device and the second pointing device and the measured line are on the same plane; and a relative position indicating section that indicates relative positions of the first pointing device and the second pointing device.

Preferably, the moving mechanism includes a turning mechanism that allows the holding device to be turnable about a position away from the first pointing device or the second pointing device; and the relative position indicating section includes an angular scale mark that indicates a turned amount by the turning mechanism of the first pointing device or the second pointing device.

Preferably, there is provided a turning mechanism that allows the holding device to be turnable about a position away from the first pointing device or the second pointing device; and the relative position indicating section is switchable between a turnable state where the holding device is turnable and a turning-regulated state where turning of the holding device is regulated along with turning of the holding device.

Preferably, the turning mechanism includes: a first turning mechanism that allows the holding device to be turnable about a first turning axis; a second turning mechanism that allows the holding device to be turnable about a second turning axis different from the first turning axis; and a coupling mechanism that couples the first turning mechanism to the second turning mechanism.

Preferably, there is further provided a main body having the sensor; the moving mechanism includes a longitudinal movement mechanism that allows the first pointing device or the second pointing device to be movable between the first position away from the main body and the second position closer to the main body than the first position so that a relative distance between the first pointing device and the second pointing device can be changed; and the relative position indicating section includes distance scale marks indicating relative distances of the first and second pointing devices in a direction connecting the first and second positions.

Preferably, the longitudinal movement mechanism includes an arm provided in the main body for allowing the first pointing device or the second pointing device to be movable between the first position and the second position; and the distance scale marks include an arm scale mark provided on the arm. Preferably, the arm includes a first arm that allows the first pointing device to be movable and a second arm that allows the second pointing device to be movable; and the distance scale marks include a first arm scale mark provided on the first arm, a second arm scale mark provided on the second arm, and a connecting scale mark connecting the first arm scale mark and the second arm scale mark. Furthermore, the distance scale marks preferably include a main body scale mark provided on the main body.

Preferably, there is further provided a main body having the sensor; and the main body includes an angle informing section that informs the detected angle, a controlling section that controls the angle informing section, and an operating section that outputs a control signal to the controlling section. Preferably, there is provided a housing device that houses the main body; and the first and second pointing devices, the holding device, the moving mechanism, and the relative position indicating section are provided in the housing device.

Preferably, the controlling section controls the angle informing section so that the angle is statically displayed.

An angle measuring device, for measuring an angle formed between a measured line connecting a first position and a second position on a body and a predetermined reference line by using a sensor capable of detecting the angle, includes: a main body having the sensor; a first pointing device for pointing the first position; a second pointing device for pointing the second position; a holding device for holding the first pointing device or the second pointing device; a moving mechanism that allows the holding device to be movable so that a line segment connecting the first pointing device and the second pointing device and the measured line are on the same plane; and a relative position indicating section that indicates relative positions of the first pointing device and the second pointing device. Preferably, the main body includes an angle informing section that informs the detected angle, a controlling section that controls the angle informing section, and an operating section that outputs a control signal to the controlling section; and the controlling section controls the angle informing section so that the angle is statically displayed.

Advantageous Effects of Invention

According to the present invention, an angle about the measured line connecting the first and second positions on a body can be measured easily. According to the wheelchair seating standard (ISO16840-1: 2006(E)), in particular, the first and second positions are often set at movable parts of a body. Thus, a considerable burden is placed on a measurer or a measured person if an angle about a measured line is measured in accordance with the above-described wheelchair seating standard. The present invention makes it possible to simplify the measurement of the measured line in accordance with the above-described wheelchair seating standard.

BRIEF DESCRIPTION OF DRAWINGS

FIG. 13A is an exploded view showing an outline of a slide movement mechanism.

FIG. 13B is an exploded view showing an outline of a slide movement mechanism.

DESCRIPTION OF EMBODIMENTS

Embodiments of the present invention will be described below with reference to the accompanying drawings.

Figure 1:
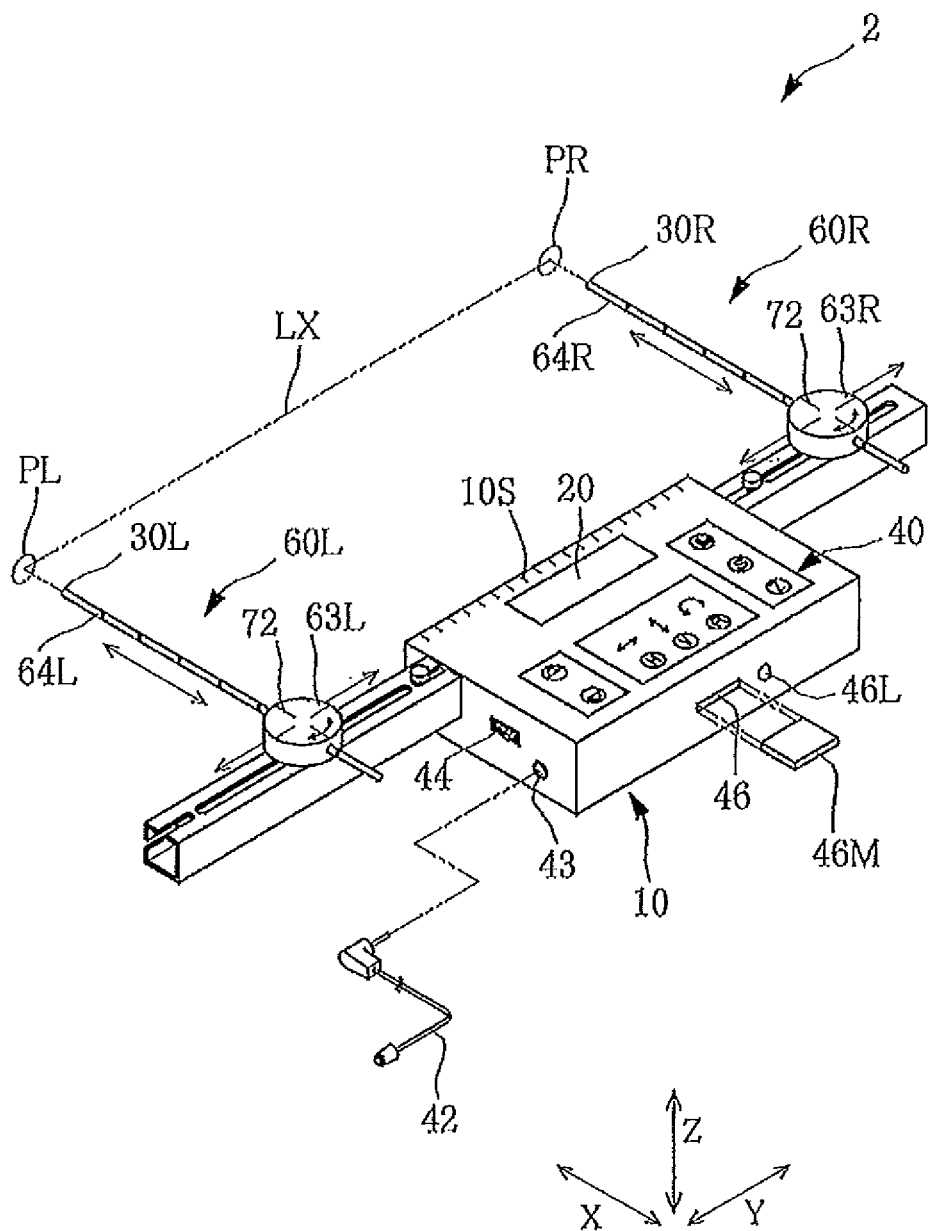
FIG. 1 is a perspective view showing an outline of an angle measuring device.
Figure 2:
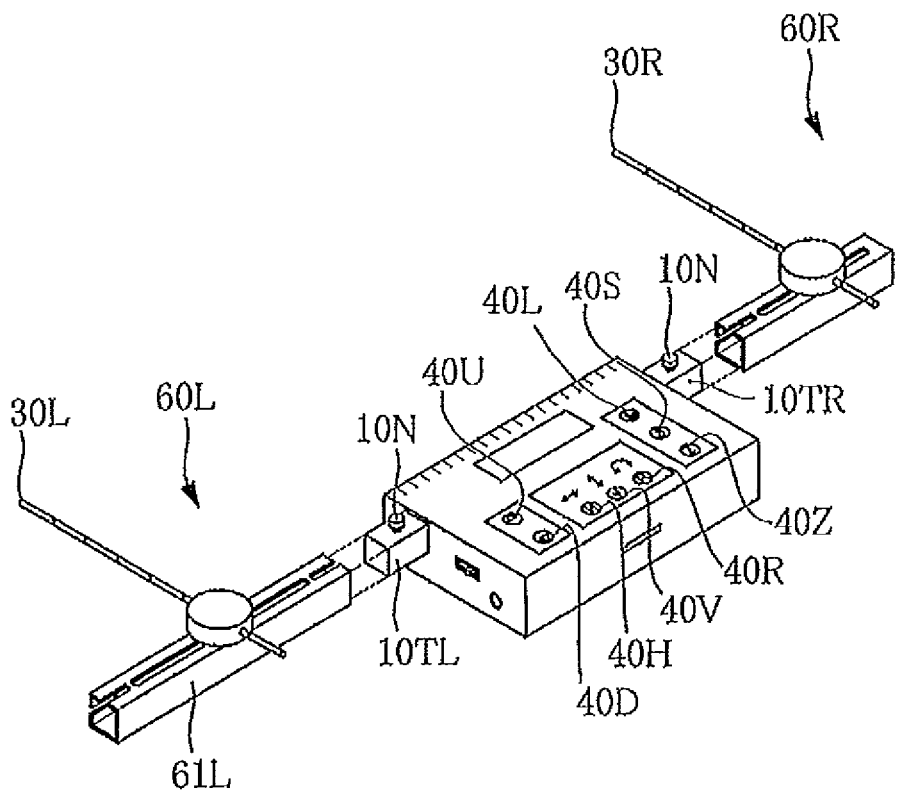
FIG. 2 is an exploded perspective view showing the outline of the angle measuring device.

As shown in FIGS. 1 and 2, an angle measuring device 2 is made to detect an angle formed between a vertical line and a measured line LX by means of an angle measuring unit having acceleration sensors. The angle measuring device 2 includes: a case 10; the angle measuring unit housed in the case 10; and first and second pointing mechanisms 30L and 30R.

The case 10 is formed in a horizontally-long cuboid shape. Hereinafter, a width (transverse) direction of the case 10, a longitudinal direction of the case 10, and a height direction of the case 10 are referred to as the X direction, the Y direction, and the Z direction, respectively. Also, an axis extending in the X direction, an axis extending in the Y direction, and an axis extending in the Z direction are referred to as the X-axis, the Y-axis, and the Z-axis, respectively.

A display 20 and an operating section 40 are provided on a top surface of the case 10. The display 20 may be a liquid crystal display, for example. The operating section 40 includes various types of operation buttons (40D, 40H, 40L, 40R, 40S, 40U, 40V, and 40Z) and a remote switch 42. The operating section 40 is provided mainly to operate the angle measuring unit. Provided on a side surface of the case 10 in the Y direction are a coupling connector 43 for the remote switch 42 and a power switch 44. Provided on one of side surfaces in the X direction are a slot 46 into which a memory card 46M can be inserted and a memory access lamp 46L. The remote switch 42 has: a switch; a cord having flexibility and provided for transmitting an electrical signal from the switch; and a connector capable of being fitted into the coupling connector 43. Note that the remote switch 42 may be of a wireless type instead of a wired type.

Furthermore, side projections 10TL and 10TR are formed on the side surfaces of the case 10 in the Y direction. A line connecting the side projection 10TR and the side projection 10TL is preferably parallel to the Y direction.

Figure 3:
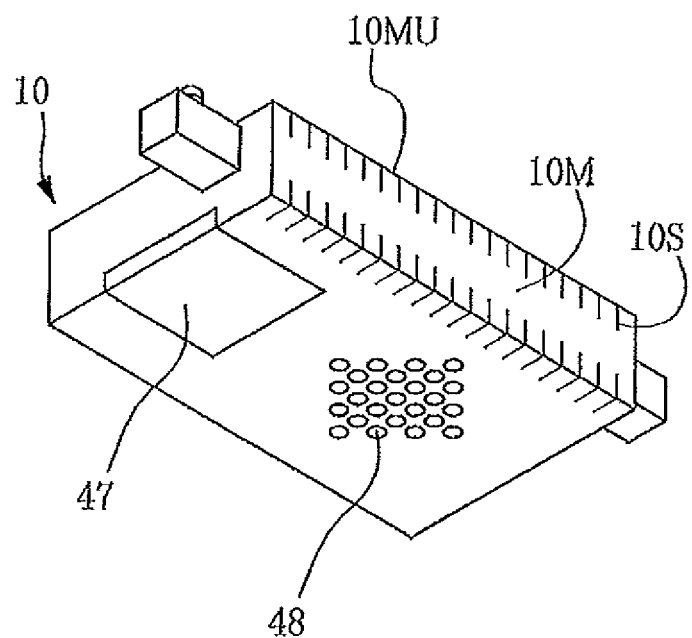
FIG. 3 is a perspective view showing an outline of the angle measuring device.
Figure 3:
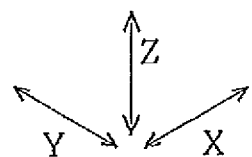

As shown in FIG. 3, a bottom cover 47 and audio output holes 48 are formed on a bottom surface of the case 10. The bottom cover 47 is provided for closing a space where an internal battery is housed. The audio output holes 48 are provided for propagating sound outputted from an internal speaker to the outside. Note that the details of the angle measuring unit will be described later.

Referring back to FIGS. 1 and 2, the angle measuring device 2 further includes: a first moving mechanism 60L that allows the first pointing mechanism 30L to be movable; and a second moving mechanism 60R that allows the second pointing mechanism 30R to be movable.

The first moving mechanism 60L will be described below while omitting the detailed description of the second moving mechanism 60R since the first moving mechanism 60L and the second moving mechanism 60R have substantially the same structure.

Figure 4:
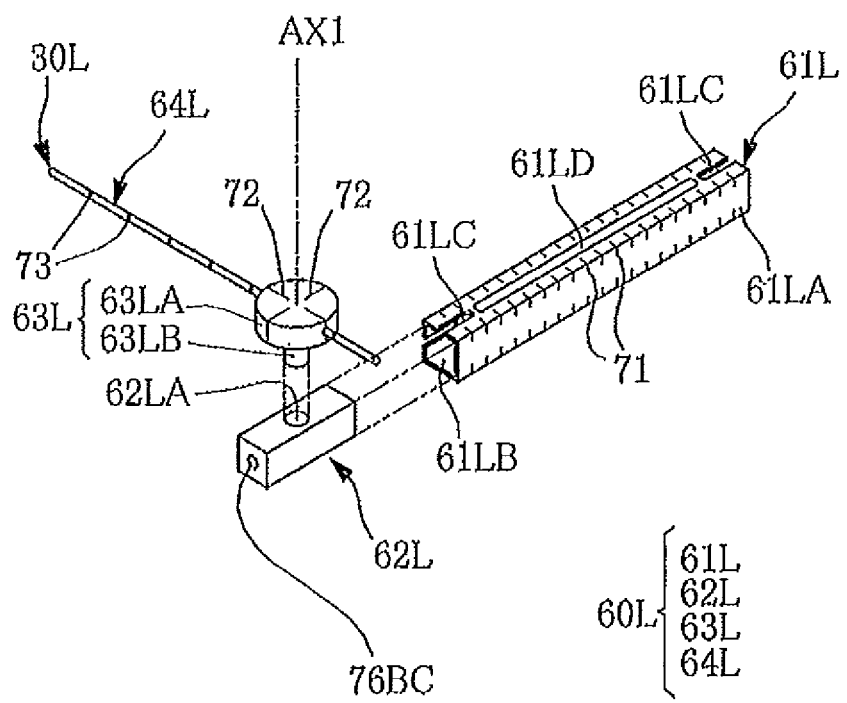
FIG. 4 is a perspective view showing an outline of a first moving mechanism.

As shown in FIGS. 2 and 4, the first moving mechanism 60L includes: an arm 61L provided on one of the side surfaces of the case 10 in the Y direction; a slide movement member 62L capable of moving along the length direction of the arm 61L; a turning member 63L fitted into the slide movement member 62L; and a measuring rod 64L slidably provided in the turning member 63L.

Figure 5:
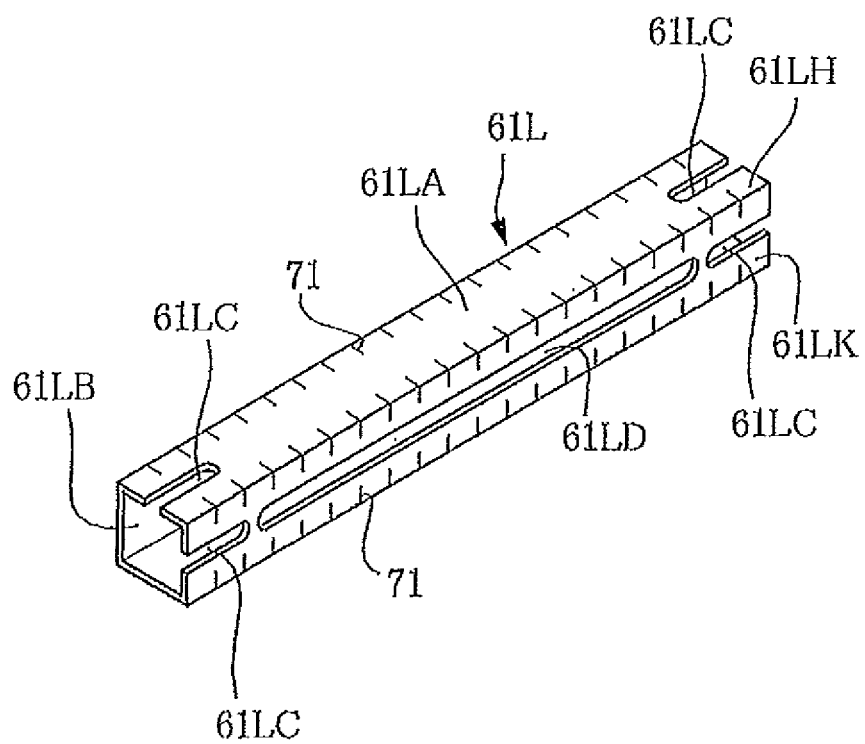
FIG. 5 is a perspective view showing an outline of an arm.
Figure 5:
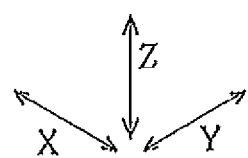

As shown in FIG. 5, the arm 61L has a quadratic prism-shaped body extending long in the Y direction. The arm 61L includes: an arm main body 61LA which is a quadratic prism-shaped body extending long in the Y direction; a slide through hole 61LB passing through the arm main body 61LA from the one end thereof to the other end thereof in the Y direction; cutout portions 61LC formed at both ends in the Y direction on side surfaces 61LH and 61LK of the arm main body 61LA; and a slide long hole 61LD formed between the cutout portions 61LC on the side surface 61LK.

Openings at both the ends of the slide through hole 61LB each have a shape capable of being fitted with the side projection 10TL. Thus, the arm 61L can be detachably attached to the case 10 by externally mounting an end of the slide through hole 61LB with respect to the side projection 10TL. Moreover, since the slide through hole 61LB and the side projection 10TL are each formed in an approximately cuboid shape, the turning of the arm 61L attached to the side projection 10TL about the Y direction is seized. Furthermore, the case 10 has fixation screws 10N. The fixation screw 10N fastens the arm 61L with the side projection 10TL via the cutout portion 61LC. The arm 61L is fixed to the case 10 by means of the fixation screw 10N. Note that the arm 61L is fastened with the side projection 10TL via the cutout portion 61LC on the side surface 61LK. Similarly, an arm 61R is detachably attached to the case 10 by means of the side projection 10TR.

As shown in FIG. 4, the slide movement member 62L is formed in an approximately cuboid shape and inserted into the slide through hole 61LB. Since the slide through hole 61LB regulates movements of the slide movement member 62L in the X and Z directions or turning thereof about the X to Z directions, the slide movement member 62L inserted into the slide through hole 61LB is consequently allowed to be movable only in the Y direction. Moreover, a circular fitting hole 62LA is formed on an upper surface of the slide movement member 62L. The slide movement member 62L is inserted into the slide through hole 61LB so that the entire fitting hole 62LA is exposed through the slide long hole 61LD.

Figure 6:
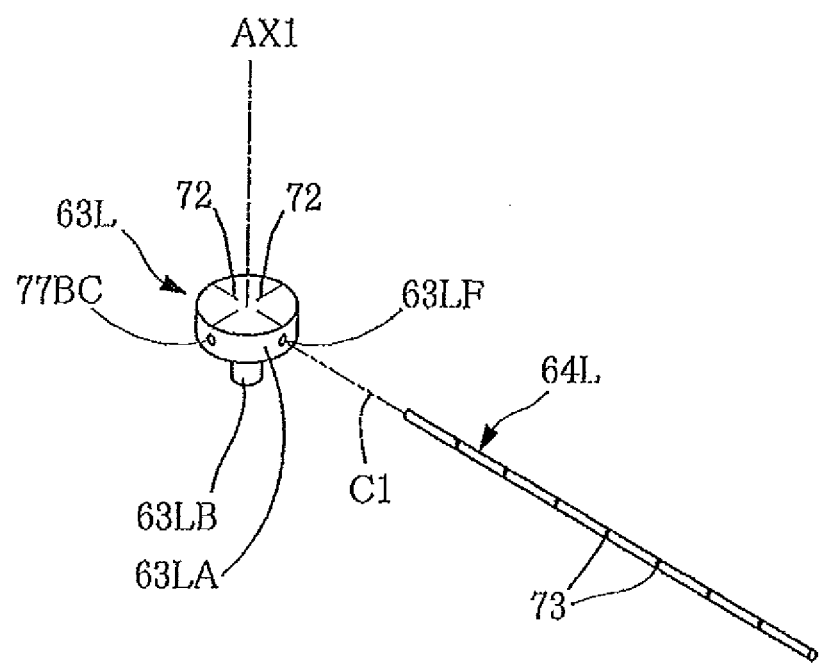
FIG. 6 is a perspective view showing an outline of a turning member and a measuring rod.

As shown in FIGS. 4 and 6, the measuring rod 64L extends in a linear fashion. The turning member 63L includes: a cylindrical rod holding section 63LA for holding the measuring rod 64L; and a cylindrical shaft portion 63LB detachably fitted into the fitting hole 62LA of the slide movement member 62L. The rod holding section 63LA includes a rod insertion hole 63LF passing through a peripheral surface thereof. The rod insertion hole 63LF extends in a linear fashion. By inserting the measuring rod 64L into the rod insertion hole 63LF, the measuring rod 64L is allowed to make a slide movement only in the direction of the length thereof. Accordingly, a tip of the measuring rod 64L functions as the first pointing mechanism 30L. The other portion of the measuring rod 64L functions as a holding mechanism. Note that the measuring rod 64L may have an extendable structure enabling extension and contraction in the longitudinal direction thereof. The extendable structure includes: a small-diameter cylindrical portion to be the first pointing mechanism 30L at a tip thereof; a large-diameter cylindrical portion having a diameter larger than that of the small-diameter cylindrical portion; and a small-diameter cylinder moving mechanism for moving the small-diameter cylindrical portion. The small-diameter cylindrical portion is housed inside the large-diameter cylindrical portion so as to be coaxial with the large-diameter cylindrical portion. The cylinder moving mechanism moves the small-diameter cylindrical portion on an axis line thereof. With such an extendable structure, a housed state where a most part of the small-diameter cylindrical portion is housed inside the large-diameter cylindrical portion and a projected state where the most part of the small-diameter cylindrical portion is projected from the large-diameter cylindrical portion can be switched therebetween.

The shaft portion 63LB is projected from a lower surface of the rod holding section 63LA so as to be coaxial with the rod holding section 63LA. Since the shaft portion 63LB and the fitting hole 62LA have approximately the same diameter, the shaft portion 63LB can be turned about itself while being fitted into the fitting hole 62LA. Note that a center line in the turning of the shaft portion 63LB preferably intersects with (for example, is perpendicular to) a center line of the rod insertion hole 63LF.

Since the slide movement member 62L is inserted into the slide through hole 61LB as described above, the tip of the measuring rod 64L is allowed to be movable in the length direction of the arm 61L. Thus, the slide movement member 62L and the arm 61L together function as a Y-direction slide movement mechanism for the first pointing mechanism 30L. Moreover, since the shaft portion 63LB is fitted into the fitting hole 62LA so as to be turnable about itself, the tip of the measuring rod 64L is allowed to be turnable about the shaft portion 63LB. Thus, the measuring rod 64L, the turning member 63L, and the slide movement member 62L together function as a turning mechanism for the first pointing mechanism 30L. Furthermore, by inserting the measuring rod 64L into the rod insertion hole 63LF, the tip of the measuring rod 64L is allowed to be movable in the length direction of the measuring rod 64L. Thus, the measuring rod 64L and the rod holding section 63LA together function as a slide movement mechanism in the length direction of the measuring rod 64L. Both the ends of the slide long hole 61LD of the first arm 61L in the Y direction can seize the shaft portion 63LB, thereby functioning as a locking mechanism for the second slide movement mechanism. Note that the first arm 61L or the like may have an extendable structure enabling the extension and contraction thereof in the longitudinal direction thereof. The extendable structure may be a structure similar to that of the measuring rod 64L.

The angle measuring device 2 further includes relative position indicating sections for indicating relative positions of the first and second pointing mechanisms 30L and 30R by the first and second moving mechanisms 60L and 60R. Examples of the relative position indicating section include a relative position indicator and an orientation maintenance mechanism. Examples of the relative position indicator includes arm scale marks 71, turning member angular scale marks 72, and measuring rod scale marks 73 (see FIG. 4). Examples of the orientation maintenance mechanism include a turning member seizing mechanism 76 (see FIG. 7A) and a measuring rod seizing mechanism 77 (see FIG. 8A).

The details of the relative position indicator and the orientation maintenance mechanism will be described next.

As shown in FIGS. 4 and 6, the arm scale marks 71 are provided on a side surface of the arm 61L for indicating relative distances from the case 10. The arm scale marks 71 are arranged in the length direction of the arm 61L (in the Y direction in the figure) at predetermined intervals (1 cm, 1 inch, or the like, for example). The arm scale marks 71 may be positioned on any of the side surfaces. Moreover, the positions where the arm scale marks 71 are provided are preferably positions visible from a measurer regardless of the orientation of the case 10. Thus, the arm scale marks 71 are preferably provided on all side surfaces (61LH, 61LK, and the like) of the arm main body 61LA, for example.

The turning member angular scale marks 72 are provided on the rod holding section 63LA for indicating a turned amount from a predetermined reference direction. The turning member angular scale marks 72 are provided at a predetermined pitch (the pitch of 90° in the figure, for example) along a circumferential direction of a turning center AX1. The positions where the turning member angular scale marks 72 are provided are preferably positions where a measurer can easily see them. For example, a preferable position is a top surface or peripheral surface of the rod holding section 63LA. From among the turning member angular scale marks 72, a turning member angular scale mark 72 parallel to a center line C1 of the rod insertion hole 63LF may be set as a reference scale mark. The reference scale mark is preferably made in a manner distinguishable from the other turning member angular scale marks 72 (for example, distinguishing with plural colors, or the like).

Figure 7A:
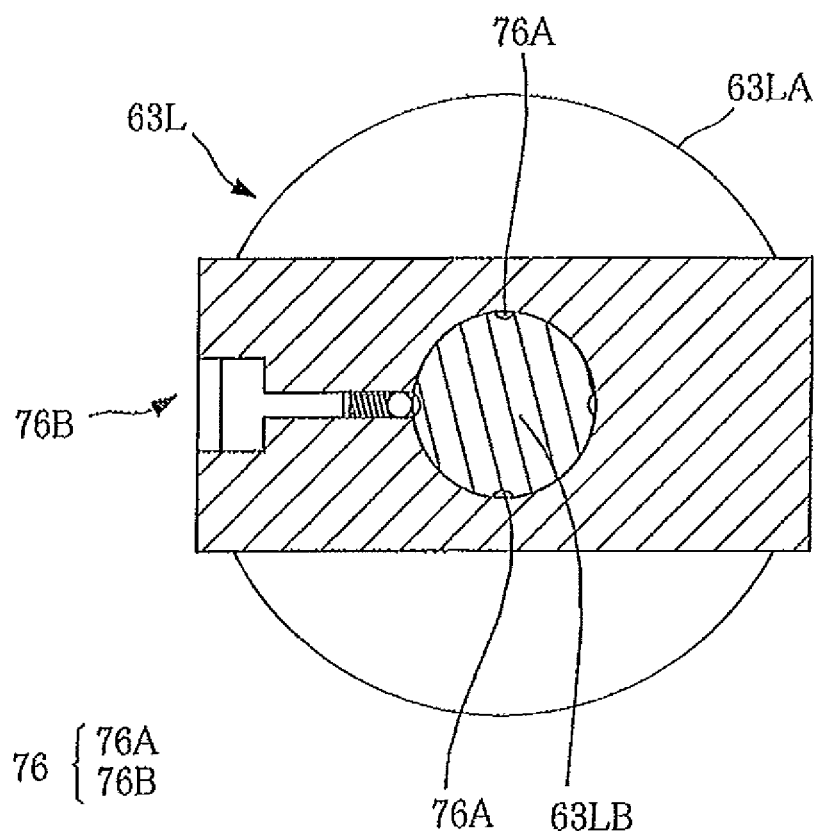
FIG. 7A is an x-y plane cross-sectional view showing an outline of a slide movement member and a shaft portion.

As shown in FIG. 7A, the turning member seizing mechanism 76 is provided so that a state where the turning of the turning member 63L is allowed and a state where the turning of the turning member 63L is regulated are switchable therebetween. The turning member seizing mechanism 76 includes: depressed portions 76A formed on a peripheral surface of the shaft portion 63LB; and a shaft portion seizing unit 76B. The depressed portions 76A are formed so as to be depressed from the peripheral surface and provided in the circumferential direction at a pitch corresponding to the turning member angular scale marks 72 (the pitch of 90° in FIG. 7A). In other words, the positions where the depressed portions 76A are formed are preferably on a plane connecting the turning member angular scale marks 72 and the turning center AX1 (see FIG. 6).

Figure 7B:
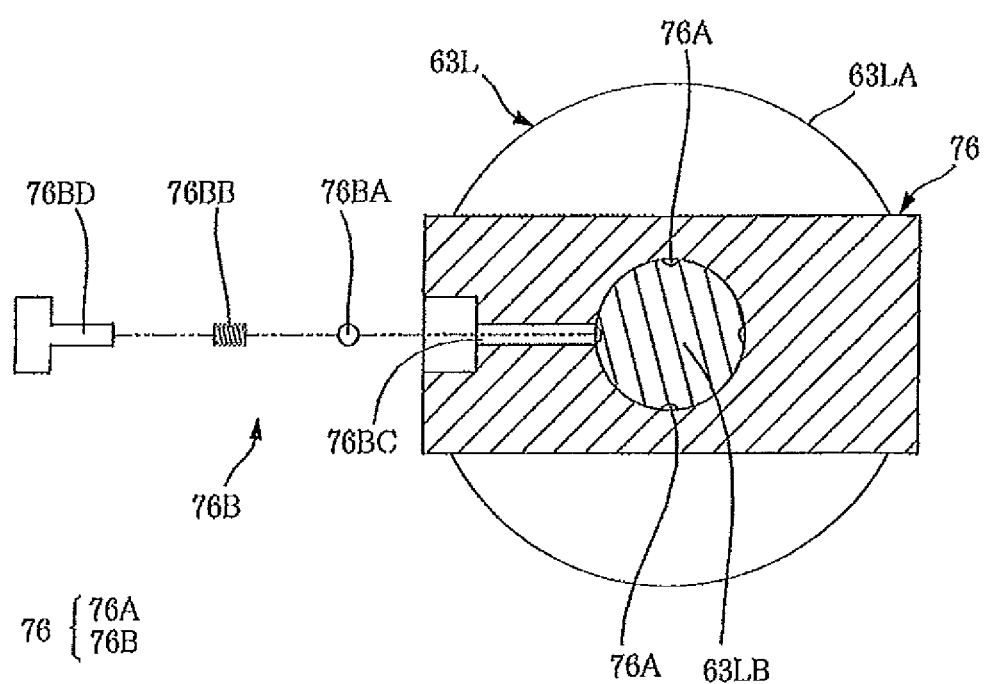
FIG. 7B is an exploded view showing an outline of a shaft portion seizing unit.

As shown in FIGS. 7A and 7B, the shaft portion seizing unit 76B includes: an engaging ball 76BA engageable with the depressed portion 76A of the shaft portion 63LB; a housing hole 76BC for housing the engaging ball 76BA; a closing screw 76BD for closing the housing hole 76BC; and a spring 76BB housed in the housing hole 76BC together with the engaging ball 76BA for biasing the engaging ball 76BA against the shaft portion 63LB. As shown in FIG. 4, one end of the housing hole 76BC is opened at a side surface of the slide movement member 62L and the other end thereof is opened to the fitting hole 62LA. With regard to the housing hole 76BC, while a bore of the opening on the side surface of the slide movement member 62L has a size just enough for the engaging ball 76BA to pass therethrough, a bore of the opening to the fitting hole 62LA is smaller than the engaging ball 76BA. Thus, the engaging ball 76BA is allowed to be movable between a projected position at which part thereof is projected from an inner peripheral surface of the fitting hole 62LA and a retracted position at which the engaging ball 76BA is retracted from the projected position. The closing screw 76BD closes the one end of the housing hole 76BC. Moreover, since the spring 76BB is provided between the engaging ball 76BA and the closing screw 76BD in the housing hole 76BC, the spring 76BB biases the engaging ball 76BA toward the projected position.

In a case where the fitting hole 62LA and the depressed portion 76A do not directly face each other, the engaging ball 76BA is pushed out by the peripheral surface of the shaft portion 63LB outwardly in the radial direction of the shaft portion 63LB. As a result, the shaft portion 63LB is allowed to be turnable about the turning center. In a case where the fitting hole 62LA and the depressed portion 76A directly face each other, on the other hand, the engaging ball 76BA is biased against the projected position, thereby locking the turning of the shaft portion 63LB by the engagement between the engaging ball 76BA and the depressed portion 76A. Thus, the orientation of the turning member 63L can be maintained. Even in a state where the movement of the shaft portion 63LB is being locked by the engagement between the engaging ball 76BA and the depressed portion 76A, if the turning member 63L is turned with a force resisting the biasing force of the spring 76BB, the engaging ball 76BA is pushed out to the retracted position, resulting in a state where the turning of the shaft portion 63LB is possible.

Figure 8A:
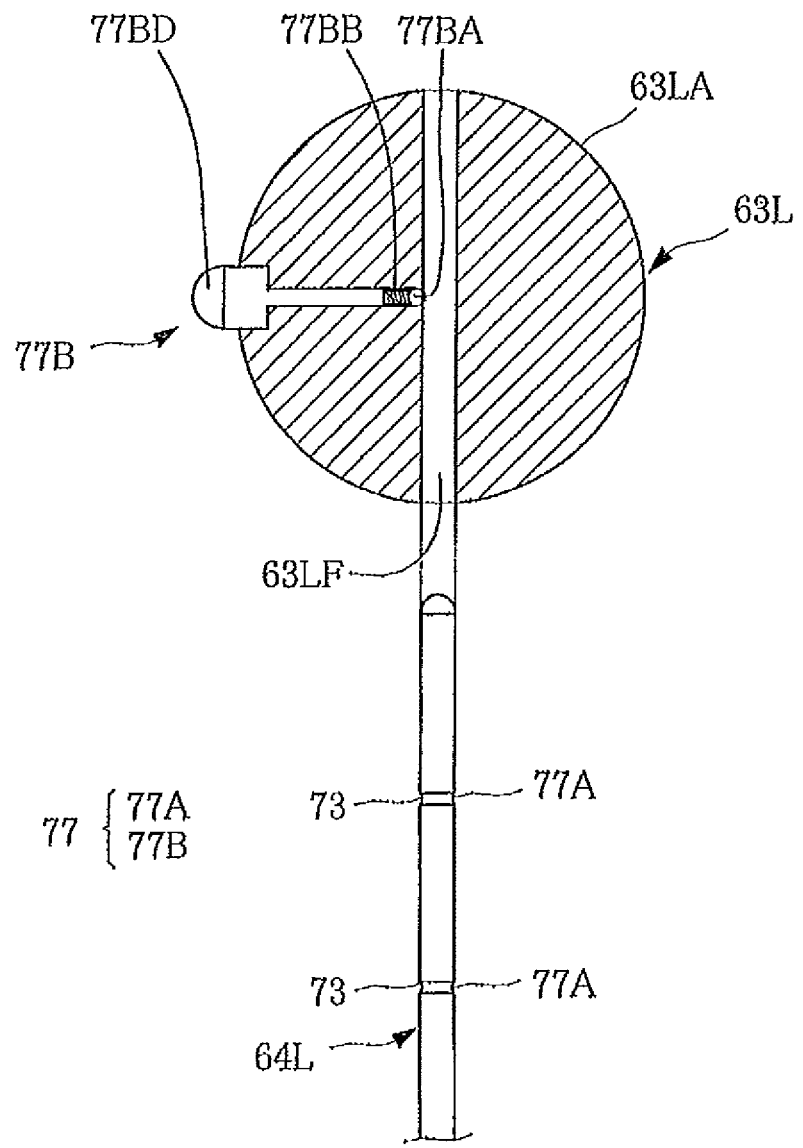
FIG. 8A is an x-y plane cross-sectional view showing an outline of a rod holding section.
Figure 8B:
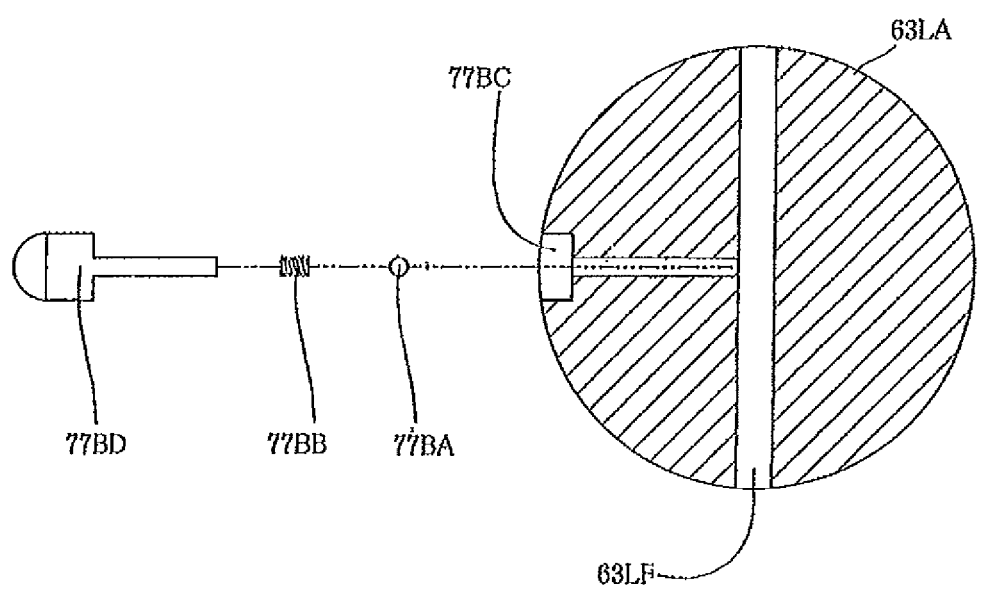
FIG. 8B is an exploded view showing an outline of a measuring rod seizing unit.

As shown in FIGS. 8A and 8B, the measuring rod scale marks 73 are provided in the longitudinal direction of the measuring rod 64L at predetermined intervals. The measuring rod seizing mechanism 77 enables the switching between a state allowing the movement of the measuring rod 64L in the length direction thereof and a state regulating the movement of the measuring rod 64L in the length direction thereof. The measuring rod seizing mechanism 77 includes: ring grooves 77A provided on the peripheral surface of the measuring rod 64L; and a measuring rod seizing unit 77B. The ring grooves 77A are provided at a predetermined pitch in the length direction of the measuring rod 64L and preferably provided so as to correspond to the measuring rod scale marks 73. In other words, it is preferred to provide the measuring rod scale marks 73 and the ring grooves 77A integrally. The measuring rod seizing unit 77B also has a structure similar to that of the shaft portion seizing unit 76B. The measuring rod seizing unit 77B includes: an engaging ball 77BA engageable with the ring groove 77A of the measuring rod 64L; a spring 77BB for biasing the engaging ball 77BA against the ring groove 77A; a housing hole 77BC for housing the engaging ball 77BA and the spring 77BB; and a closing screw 77BD for closing the housing hole 77BC.

In a case where the housing hole 77BC and the ring groove 77A do not directly face each other, the engaging ball 77BA is pushed out by the peripheral surface of the measuring rod 64L outwardly in the radial direction of the rod holding section 63LA. As a result, the measuring rod 64L is allowed to make a slide movement in the length direction thereof in the rod insertion hole 63LF. In a case where the housing hole 778C and the ring groove 77A directly face each other, on the other hand, part of the engaging ball 77BA is projected from the rod insertion hole 63LF by the biasing force of the spring 77BB. Thus, the slide movement of the measuring rod 64L in the length direction thereof is locked by the engagement between the engaging ball 77BA and the ring groove 77A. Thus, the relative position of the measuring rod 64L to the turning member 63L can be maintained. Even in a state where the slide movement of the measuring rod 64L is being locked by the engagement between the engaging ball 77BA and the ring groove 77A, if the measuring rod 64L is moved with a force resisting the biasing force of the spring 77BB, the engaging ball 77BA is pushed outwardly in the radial direction, resulting in a state where the slide movement of the measuring rod 64L is possible.

Note that the arm 61L may have a turning member seizing mechanism having a structure similar to that of the measuring rod seizing mechanism 77. The turning member seizing mechanism includes: a seizing groove provided on an inner peripheral surface of the arm main body 61LA; and a seizing unit capable of being seized by the seizing groove. The seizing unit has a structure similar to that of the measuring rod seizing unit 77B. Moreover, the seizing groove is provided in a similar manner to that of the ring groove 77A.

Figure 9:
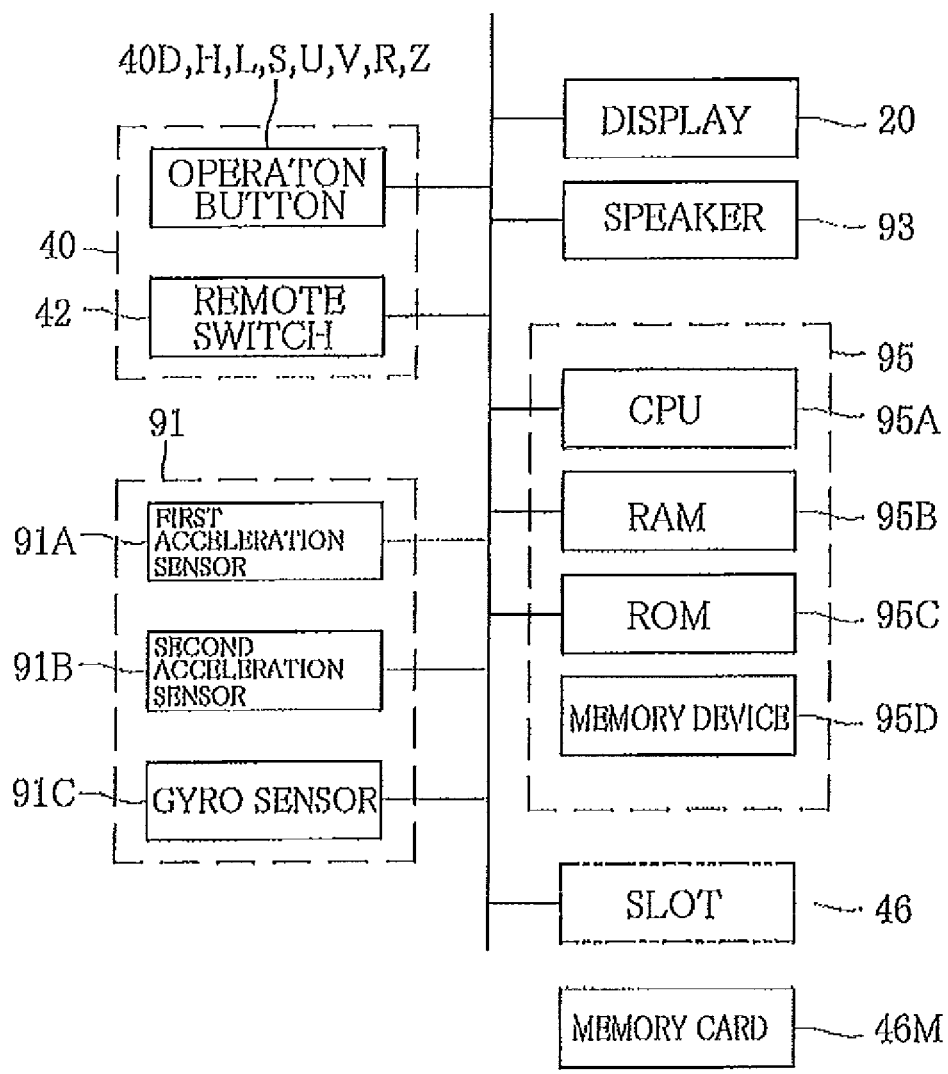
FIG. 9 is a connection diagram showing an outline of an angle measuring unit.

With reference to FIG. 9, an angle measuring unit 90 will be described next.

The angle measuring unit 90 includes: the display 20; the operating section 40; the slot 46; the memory access lamp 46L; a sensor unit 91; a speaker 93; and a controller 95.

The controller 95 includes: a CPU 95A; a RAM 95B; a ROM 95C; and a memory device 95D. The CPU 95A is what is called a central processing unit, and various types of program are executed thereon so as to implement various types of function of the controller 95. The RAM 95B is used as a work area for the CPU 95A. The ROM 95C stores a basic OS to be executed in the CPU 95A. The memory device 95D is formed by a hard disk drive containing a magnetic disk, a disk device accommodating a CD, a DVD, or a BD, a non-volatile semiconductor flash memory device, and the like. The memory device 95D stores various types of program to be executed in the CPU 95A. Note that the memory device 95D may be omitted.

The respective sections of the angle measuring unit 90 are electrically connected to each other via a bus 98. The memory card 46M inserted into the slot 46 is electrically connected to the bus 98 via the slot 46.

The sensor unit 91 is designed to measure a predetermined angle on the basis of a set reference line. The sensor unit 91 includes: a first acceleration sensor 91A; a second acceleration sensor 91B; and a gyro sensor 91C, and outputs sensing signals from the respective sensors 91A to 91C. The first acceleration sensor 91A detects an angle formed between a first sensor reference axis (z-axis) and the vertical line. The second acceleration sensor 91B-detects an angle formed between a second sensor reference axis (x-axis) and the vertical line. The gyro sensor 91C detects an angular velocity about the Z-axis. Note that the sensor unit 91 may be a triaxial acceleration sensor or a six-axis sensor.

When the operating button 40 (such as 40D) is operated, it outputs an operation signal corresponding to that button. The controller 95 controls the respective sections via the bus 98.

An action of the controller 95 will be described next.

First, when the power switch 44 (see FIG. 1) is turned ON, an electric power of the internal battery is supplied to the respective sections. If the controller 95 detects an operation signal from the H (horizontal) button 40H, the mode is transferred to a horizontal angle measuring mode. In the horizontal angle measuring mode, the controller 95 first reads a sensing signal from the acceleration sensor 91A. The controller 95 then calculates an angle formed between the z-axis and the vertical line (horizontal angle) on the basis of the read sensing signal. Thereafter, the controller 95 displays the calculated horizontal angle on the display 20.

If the controller 95 detects an operation signal from the V (vertical) button 40V, the mode is transferred to a vertical angle measuring mode. In the vertical angle measuring mode, the controller 95 first reads sensing signals from the acceleration sensors 91A and 91B. The controller 95 then calculates an angle formed between the z-axis and the vertical line (first vertical angle component) and an angle formed between the x-axis and the vertical line (second vertical angle component) on the basis of the read sensing signals. Thereafter, the controller 95 displays the calculated first and second vertical angle components (collectively referred to as a vertical angle) on the display 20.

If the controller 95 detects an operation signal from the R (rotation) button 40R, the mode is transferred to a rotation angle measuring mode. In the rotation angle measuring mode, the gyro sensor 91C is used. First, by means of the controller 95, indication expressing that a rotation axis for measuring a rotation angle is to be measured is made on the display 20.

Furthermore, the controller 95 reads a sensing signal from the gyro sensor 91C and sets the rotation axis for measuring the rotation angle on the basis of this sensing signal. Thereafter, the measurement of the rotation angle is started. Specifically, the controller 95 first reads a sensing signal from the gyro sensor 91C. Thereafter, the controller 95 performs an integral treatment on the basis of the read sensing signal to calculate the rotation angle. The controller 95 then displays the calculated rotation angle on the display 20. The thus obtained rotation angle is an angle about the Y-axis with the Y direction (or the X direction) of the case 10 when the rotation axis for measuring the rotation angle is set being used as the reference line.

In each of the measuring modes, if the controller 95 detects an operation signal from the S button 408, it stores in the memory card 46M horizontal angle data based on the sensing signal read upon the detection of the operation signal. Moreover, the controller 95 makes the memory access lamp 46L lit or flashing while the horizontal angle data is being stored. If the storing of the horizontal angle is properly done in the memory card 46M, the controller 95 then activates the speaker 93 for outputting a predetermined sound.

When an operation signal from the remote switch 42 is detected, the controller 95 performs control similar to that upon the detection of an operation signal from the S button 408. In a case where an angle is measured by the angle measuring device 2, it is often necessary to hold the case 10, the arm 61L, or the like with both hands. In such a case, it is difficult to operate the S button 408. Thus, by employing the remote switch 42, it becomes possible to hold the case 10, the arm 61L, or the like while gripping the remote switch 42. As a result, an operation such as the storing of the measured data is facilitated.

Furthermore, the operation buttons 40D and 40U are used when inputting respective set values, and the operation button 40Z is used when manually setting a measurement start condition.

Returning to FIG. 1, a description will next be given of a method for measuring a predetermined angle about the measured line LX connecting a first position PL and a second position PR by using the angle measuring device 2.

First, the power is turned ON so as to activate the angle measuring device 2. Thereafter, the H button 40H is pressed down. If the controller 95 detects an operation signal from the H button 40H, the mode is transferred to the horizontal angle measuring mode. The measured horizontal angle is displayed on the display 20.

Next, the first and second moving mechanisms 60L and 60R are used to set the first pointing mechanism 30L at the first position PL and set the second pointing mechanism 30R at the second position PR (hereinafter, referred to as a site pointing step).

The following first to third steps are performed during the site pointing step.

First, the slide movement of the measuring rod 64L and 64R are made in the length direction thereof so that the projected amounts of both the measuring rods 64L and 64R are equal to each other (first step). The projected amounts of the measuring rods herein refer to distances from the turning centers AX1 (see FIG. 6) to the tips of the measuring rods (i.e., the first and second pointing mechanisms 30L and 30R), respectively.

Second, the measuring rods 64L and 64R are turned with respect to the respective turning centers AX1 (see FIG. 6) so that the orientations of the measuring rods 64L and 64R are symmetrical with respect to the X direction (second step). Note that the first step and the second step may be transposed.

Because of the first and second steps, the line connecting the first and second pointing mechanisms 30L and 30R becomes perpendicular to the first sensor reference axis (z-axis).

Third, the slide movement of the turning member 63L is made in the Y direction so that the first pointing mechanism 30L points the first position PL and the second pointing mechanism 30R points the second position PR. As a result, the line segment connecting the first pointing mechanism 30L and the second pointing mechanism 30R becomes parallel to the line segment connecting the first position PL and the second position PR, i.e., the measured line LX.

After the site pointing step, if the controller 95 detects an operation signal from the S button 40S, it stores the horizontal angle based on the read sensing signal in the RAM 95B upon the detection of the operation signal. Moreover, if the storing of the horizontal angle is properly done in the memory card 46M, the controller 95 then activates the speaker 93 for outputting a predetermined sound.

In this manner, the horizontal angle in the measured line LX can be measured easily. Note that the measurement of the rotation angle is also performed in a manner similar to the measurement of the horizontal angle. In the case of the measurement of the vertical angle, the line connecting the first and second pointing mechanisms 30L and 30R is set to be perpendicular to the first sensor reference axis (z-axis) and the second sensor reference axis (x-axis), i.e., parallel to the y-axis in the first and second steps.

If the mode in which the first and second pointing mechanisms 30L and 30R are movable is limited to the slide movements in the X direction and the Y direction, it is impossible to measure the predetermined angle in the case of an extremely short measured line LX as compared to the length of the case 10 in the Y direction or an extremely long measured line LX. According to the angle measuring device 2, the first and second pointing mechanisms 30L and 30R can turn about positions away from themselves, thereby widening a measurable range for the measured line LX. Moreover, the turning member angular scale marks 72 and the turning member seizing mechanism 76 are included according to the angle measuring device 2, thereby reliably creating a state where the orientations of the measuring rods 64L and 64R are symmetrical with respect to the X direction. Thus, the predetermined angle about the measured line LX can be accurately measured even when the measuring rod 64L and the arm 61L are obliquely crossed each other. Similarly, the measuring rod scale marks 73 and the measuring rod seizing mechanism 77 are included according to the angle measuring device 2, thereby reliably creating a state where the projected amounts of both of the measuring rods 64L and 64R are equal to each other.

Figure 10:
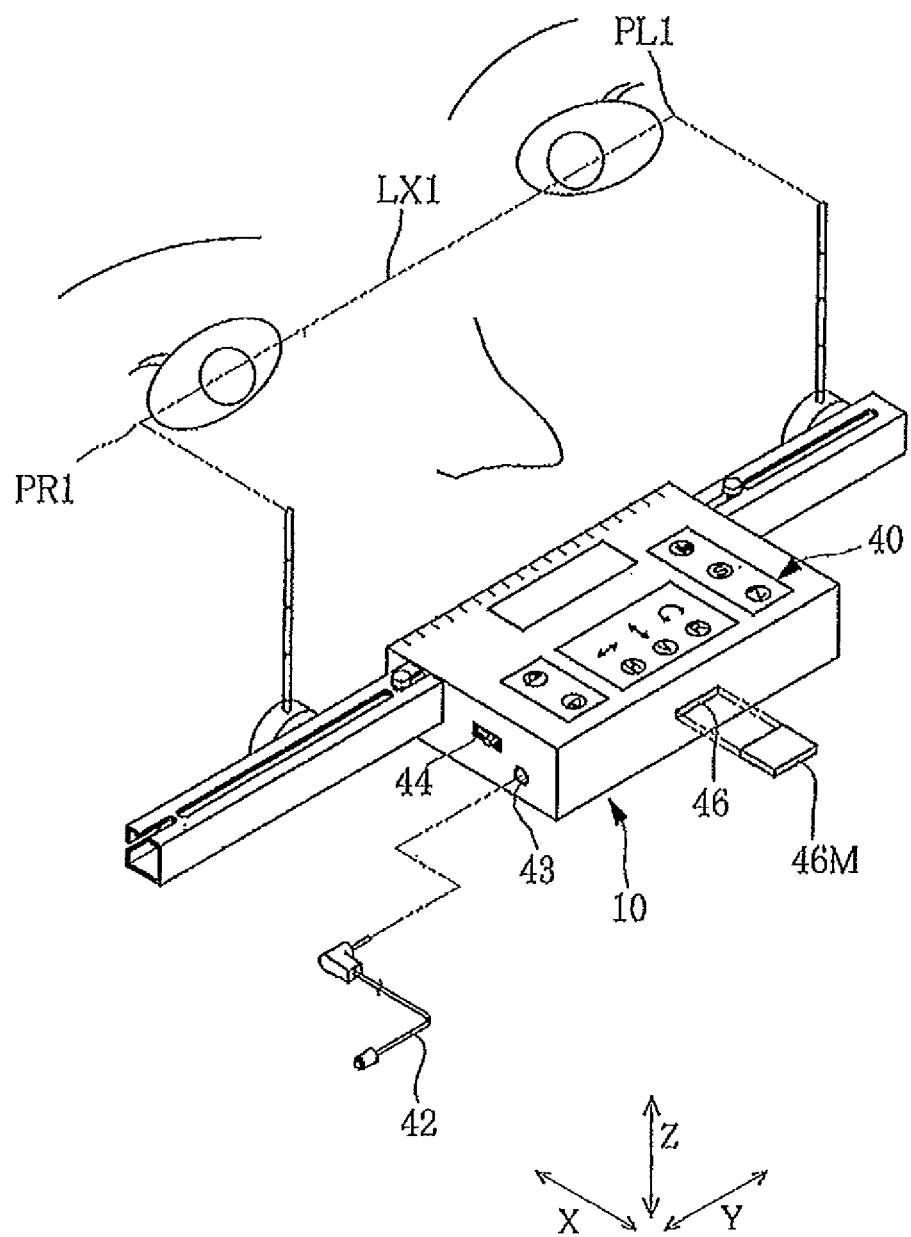
FIG. 10 is a perspective view showing an outline of an angle measuring device.

Moreover, since the cutout portions 61LC are provided on both of the side surfaces 61LH and 61LK (see FIG. 5) in the angle measuring device 2, transition between a state where the measuring rods 64L and 64R are parallel to an x-y plane (see FIG. 1) and a state where the measuring rods 64L and 64R are parallel to a y-z plane (see FIG. 10) becomes possible. For example, in a case where the direction of a measured line LX1 connecting a right eye corner PR1 and a left eye corner PL1 is measured, if the angle measuring device 2 in the state of FIG. 1 is used as it is, the angle measuring device 2 (especially the measuring rods 64L and 64R and the case 10) is positioned in front of the eyes of the measured person. Therefore, unnecessary stress will be given to the measured person during the measurement. Thus, by setting the measuring rods 64L and 64R to be parallel to the y-z plane (see FIG. 10), the angle measuring device 2 is prevented from being positioned in front of the eyes of the measured person, thereby eliminating unnecessary stress on the measured person during the measurement.

Furthermore, since the arm scale marks 71 are provided (see FIG. 5) according to the angle measuring device 2, it is possible to measure both of the angle about the measured line LX and the length of the measured line LX. For example, when the measuring rod 64L is perpendicular to the arm 61L, i.e., when both of the measuring rods 64L is directed in the X direction, the length of the measured line LX can be obtained by adding the length of the case 10 in the Y direction to lengths read from both of the arm scale marks 71. Note that an indicator indicating the length of the case 10 in the Y direction may be provided on the case 10 or the like. Even in a state where the measuring rod 64L and the arm 61L are obliquely crossed each other, it is possible to measure the length of the measured line LX by using the values read from the arm scale marks 71, the turning member angular scale marks 72, and the measuring rod scale marks 73.

Although the tips of the measuring rods 64L and 64R are used as the first and second pointing mechanisms 30L and 30R in the above-described embodiment, the present invention is not limited thereto. Of the side surfaces of the case 10, an upper edge line 10MU on a side surface (hereinafter, referred to as a measuring surface) 10M on the side of the measured line LX may be used as the first and second pointing mechanisms (see FIG. 3). In this case, the orientation of the case 10 is adjusted so that the measured line LX connecting the first position PL and the second position PR is perpendicular to each sensor shaft. By executing the predetermined measuring mode in such a state, the predetermined angle about the measured line LX can be measured. Note that the measured line LX and the measuring surface 10M may be in contact with each other or may be apart from each other when executing the predetermined measuring mode. Obviously, the upper edge line 10MU may be used as the first pointing mechanism, and the tip of the measuring rod 64L or the like attached to the case 10 may be used as the second pointing mechanism.

Furthermore, the case 10 may have case scale marks 10S (see FIG. 1). Of the edge lines forming the measuring surface 10M, the case scale marks 10S are provided along edge lines 10ML and 10MU extending in the Y direction. The position where the case scale marks 10S are formed may be on a top surface or a bottom surface aside from the measuring surface 10M. The case scale marks 10S are preferably provided so as to connect the arm scale marks 71 provided on the arm 61L and the arm scale marks 71 provided on the arm 61R. Additionally, the case scale marks 10S and the arm scale marks 71 (see FIG. 4) may be apart from each other in another direction (for example, the X direction or the Z direction) as long as they are in synchronization with each other in the Y direction. With such scale marks 10S and 71, it is possible to easily obtain the position of a midpoint between the first position PL and the second position PR. For example, in a case where an abdominal line is measured, the tips of both the measuring rods are first set at the right ASIS (anterior superior iliac spine) and at the left ASIS, respectively, so as to obtain the midpoint between the right ASIS and the left ASIS. Second, the tips of both the measuring rods are set at the obtained midpoint and the lower end of the sternum, respectively. In this way, even an angle about the abdominal line can be obtained easily.

Figure 11:
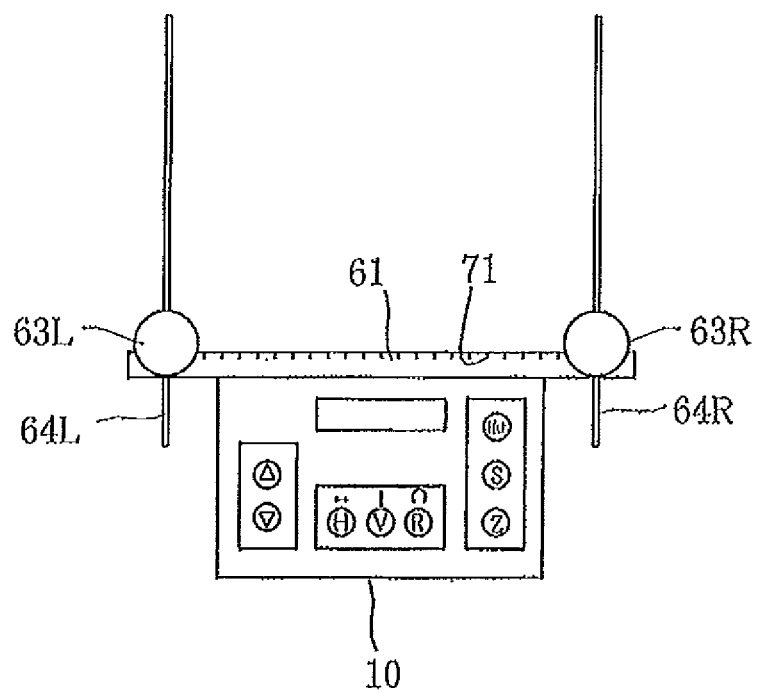
FIG. 11 is a plan view showing an outline of an angle measuring device.

Although the arms 61L and 61R are provided on both of the side surfaces of the case 10 in the Y direction in the above-described embodiment, the present invention is not limited thereto. As shown in FIG. 11, the arm 61 extending in the Y direction may be provided on the measuring surface 10M. The arm 61 is preferably attached to the case 10 in a detachable manner. This makes it possible to measure the measured line LX shorter than the length of the case 10 in the Y direction and to facilitate the above-described measurement of the abdominal line (see FIG. 10).

Figure 12:
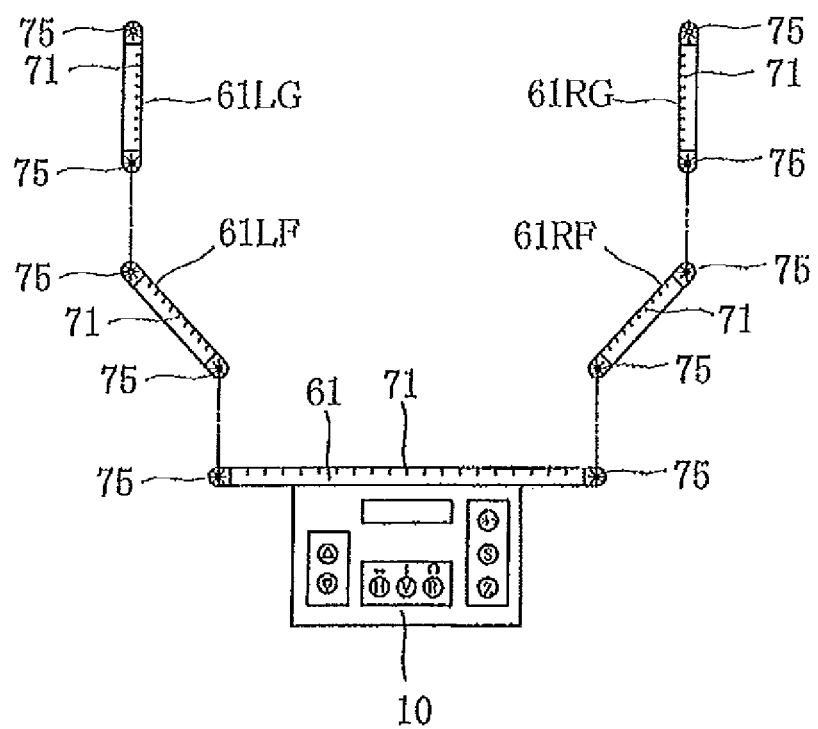
FIG. 12 is an exploded view showing an outline of an angle measuring device.
Figure 18A:
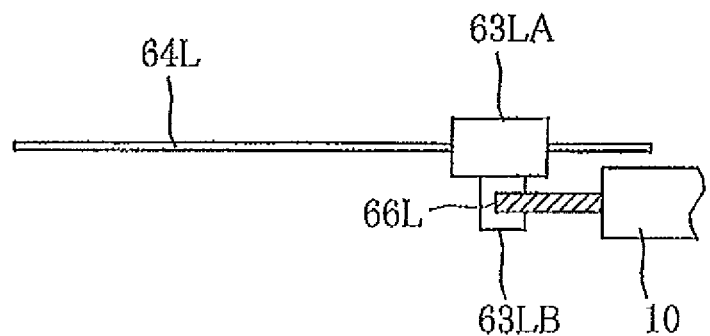
FIG. 18 is an explanatory diagram showing an outline of a method for measuring a movable range of a hip joint.
Figure 18B:
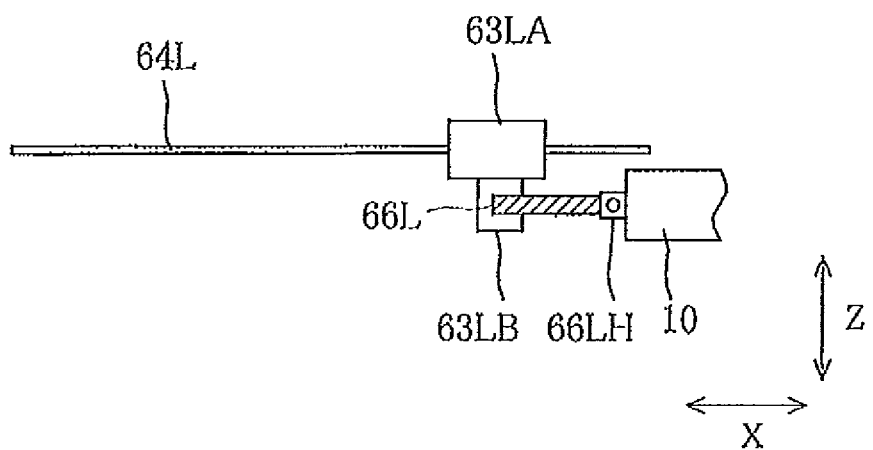

Furthermore, turning arms 61LF and 61LG and 61RF and 61RG may be attached to both the ends of the arm 61 (see FIG. 12). The turning arms 61LF and 61RF are coupled to the arm 61 in a turnable manner via a first coupling mechanism (a hinge or the like). The turning arms 61LG and 61RG are coupled to the turning arms 61LF and 61RF in a turnable manner via a second coupling mechanism (a hinge or the like). Although not shown in the figure, the measuring rod 64L, the turning member 63L, and the like (see FIG. 11) may be provided on predetermined positions of the arms 61, 61LF and 61LG, and 61RF and 61RG. As a result, in a state where the arm 61 and the turning arm 61LF or the like form a straight line, an extremely long measured line LX can be measured. Also, in a state where the direction of the turning arm 61LF or the like and the direction of the arm 61 cross each other, it becomes possible to measure even a line segment (the measured line LX) for which a direct measurement from the outside is impossible, such as the direction of the pelvis inside the body. Furthermore, since the turning arm 61LF or the like is foldable, it is easy to be stored. Moreover, angular scale marks 75 similar to the turning member angular scale marks 72 may be provided at end portions of the arm 61, the turning arm 61LF, and the like. Furthermore, the first and second coupling mechanisms may each have a turning member seizing mechanism similar to the turning member seizing mechanism 76. In addition, the above-described arm scale marks 71 may be provided on the arm 61, the turning arm 61LF, and the like.

Although the turning arms 61LF and 61LG and 61RF and 61RG are used together with the case 10 and the arm 61 in the above-described embodiment, the present invention is not limited thereto. The case 10 and the arm 61 may be employed while omitting all of the turning arms 61LF to 61RG, or part of the turning arms 61LF to 61RG. Examples of an embodiment omitting part of the turning arms 61LF to 61LG includes: a case where the case 10, the arm 61, and the turning arm 61LF are employed while omitting the turning arms 61LG and 61RF and 61RG; and a case where the case 10, the arm 61, and the turning arms 61LF and 61LG are employed while omitting the turning arms 61RF and 61RG.

When it is desired to measure an angle about a measured line in order to measure a physical posture, particular sites of the skeleton are often used as first and second sites. Depending on a posture of the measured person (such as a person seated on a wheelchair) or a body shape of the measured person (for example, such as a pyknic type), however, an element (wheelchair) or a site of the body in the vicinity of the first and second sites may possibly interfere with the case 10. In a case where the turning arm as described above is provided, however, it is possible to circumvent the wheelchair or the like by combining the number of the turning arms and the turning states of the turning arms. Thus, an angle about a measured line can be measured easily with such an angle measuring device.

Figure 13C:
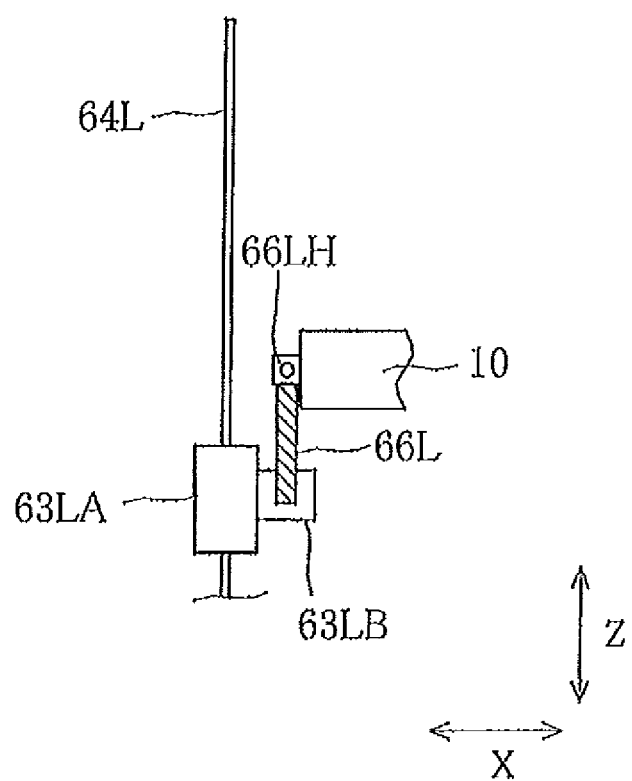
FIG. 13C is an exploded view showing an outline of the slide movement mechanism.

Although the slide movement member 62L and the arm 61L are used as the Y-direction slide movement mechanism for the first pointing mechanism 30L in the above-described embodiment, the present invention is not limited thereto. A rail 66L in the form of a plate parallel to the x-y plane and a guide groove 67L provided on a peripheral surface of the shaft portion 63LB (see FIG. 13A) may be used as the Y-direction slide movement mechanism for the first pointing mechanism 30L. By fitting the guide groove 67L to the rail 66L, the shaft portion 63LB is allowed to be movable along the rail 66L. This makes the configuration of the Y-direction slide movement mechanism for the first pointing mechanism 30L simple. Note that scale marks similar to the arm scale marks 71 may be provided on the rail 66L. Furthermore, the rail 66L and the case 10 may be connected to each other by means of a hinge 66LH so that it is possible to transfer between a state where the rail 66L is parallel to the x-y plane (see FIG. 13B) and a state where the rail 66L is parallel to the y-z plane (see FIG. 13C). These are applied also to the Y-direction slide movement mechanism for the second pointing mechanism 30R.

As described above, since the orientation of the case 10 is not always constant when measuring the predetermined angle about the measured line LX, there is a case where it is difficult for the measurer to visually check the indication on the display 20. Thus, it is preferred to have a HOLD function as will be described next. If the controller 95 detects an operation signal from the HOLD button 40L prior to the detection of the operation signal from the button 40H, 40V, or 40R, the HOLD function is enabled during the measuring mode to be performed thereafter.

An operation in the case where the HOLD function is being enabled will be described taking the horizontal angle measuring mode as an example. In the horizontal angle measuring mode, the controller 95 first reads a sensing signal from the sensor unit 91. The controller 95 then calculates the horizontal angle on the basis of the read sensing signal. Next, the controller 95 displays the calculated horizontal angle on the display 20. Here, if the controller 95 detects the first operation signal from the S button 40S, it stores the horizontal angle based on the read sensing signal in the RAM 95B upon the detection of the operation signal and maintains a state where that horizontal angle is being displayed on the display 20 (HOLD display state). Thereafter, if the controller 95 detects the second operation signal from the S button 40S, it stores the horizontal angle in the HOLD display state in the memory card 46M. If the storing of the horizontal angle is properly done in the memory card 46M, the controller 95 then activates the speaker 93 for outputting the predetermined sound and ends the HOLD display state.

In a case where the HOLD function is used, transition timing to the HOLD display state may be when the first operation signal from the S button 40S is detected as described above or when a predetermined waiting time is passed since the detection of the first operation signal from the S button 40S. This waiting time may be stored beforehand in the ROM 95C or may be set by an operation of the operating section 40. In a case where the waiting time has been set, advance notice for the start of the transition to the HOLD display state may be performed. Modes to perform the advance notice include a case where the remaining time until the transition to the HOLD display state is displayed on the display 20; a case where a countdown is performed by the speaker 93; and a case where the remaining time is read aloud by vocal guidance, and any one of them is possible. As an example of the countdown by the speaker 93, the internal speaker may be sounded by the second until the start of the transition to the HOLD display state starting from some remaining time (e.g., 3 seconds), for example.

Instead of the HOLD function, the controller 95 may display a measured value on the display 20 while reading aloud the measured value by voice.

Moreover, instead of providing the display 20 on the case 10, another display case including the display 20 may be connected to the case 10 with a flexible cable for connecting the case 10 and the display case.

When the controller 95 detects an operation signal from the remote switch 42, it may perform control similar to that when an operation signal from the HOLD button 40L is detected. This makes it possible to display the measured data statically while maintaining the holding of the case 10, the arm 61L, or the like. As a result, the measurer can check the statically-displayed measured data after the measurement.

Note that a function for computing two measured angles may be given. For example, the controller 95 measures a first horizontal angle and stores it in the RAM 95B (see FIG. 9), and then measures a second horizontal angle and stores it in the RAM 95B. Thereafter, the controller 95 computes a difference between the first horizontal angle and the second horizontal angle and may display the computed result on the display 20. Alternatively, the controller 95 may subtract "the obtained angle" from "90°" and display the calculated angle on the display 20.

Moreover, in a case where the controller 95 detects that each sensor has a failure or an angle outside the measurement range has been obtained, it may output an error message indicating that to the display 20.

As shown in FIG. 1, the case 10 may have a measuring direction indicator indicating the direction of the measured line LX with respect to the case 10. The measuring direction indicators are provided on the side of the measuring surface 10M on the top surface of the case 10. Although FIG. 1 shows a case where the case scale marks 10S are used as the measuring direction indicators, the present invention is not limited thereto.

Figure 14:
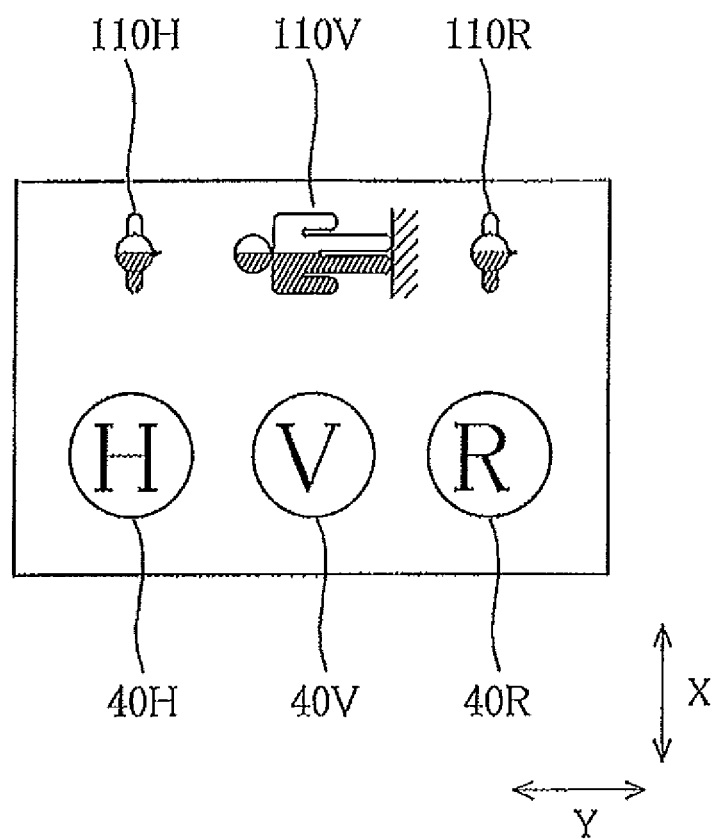
FIG. 14 is a plan view showing an outline of an indicator that resembles a human.

In the vertical angle measuring mode, in the meantime, if a measurement is performed with the orientation of the case 10 being reversed in the X to Z directions, it is impossible to measure a vertical angle accurately. Thus, as an indicator indicating the V button 40V, it is preferred to employ an indicator indicating the vertical direction in the vertical angle measuring mode. For example, as shown in FIG. 14, an indicator 110V that resembles a human may be used. The indicator 110V is an indicator that resembles a standing measured person as viewed from the top surface (x-y plane) of the case 10 in the vertical angle measurement and located in the vicinity of the V button 40V. Moreover, the indicator 110V also includes an indicator indicating the correct orientation about the vertical direction of the measured person (for example, an indicator indicating the lower side or the ground). Furthermore, according to the wheelchair seating standard (ISO16840-1: 2006(E)), the measuring directions are defined to be a frontal plane, a transverse plane, and a sagittal plane. The sagittal plane is defined to be a plane as viewed from the right side of the measured person. Thus, an indicator indicating the measuring direction with respect to the measured person may be provided on that indicator 110V or the like. With regard to the sagittal plane, in particular, it is more likely to be measured in a left-right reversal manner. Thus, there is provided an indicator such that a portion indicating the measuring direction is emphasized more as compared to the other portion of the indicator 110V (for example, the portion indicating the measuring direction is shown in red and the other portion is shown in white in FIG. 14). Needless to say, also in the vicinity of another button (the H button 40H or the R button 40R), an indicator 110H or 110R indicating the correct orientation of the case 10 in the measuring mode corresponding to that button may be provided.

Figure 15:
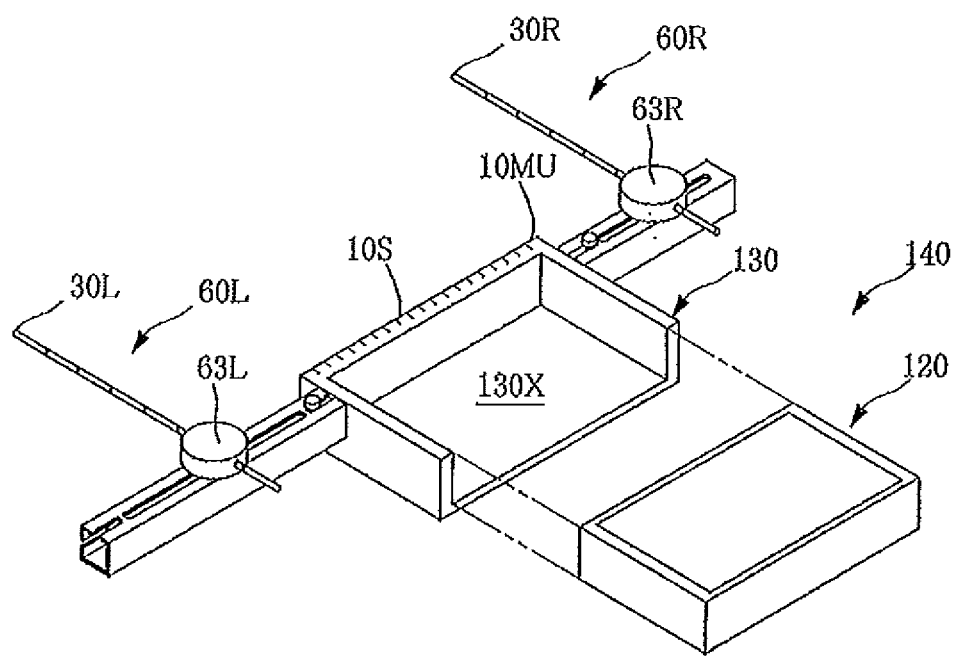
FIG. 15 is a perspective view showing an outline of an angle measuring device.
Figure 16:
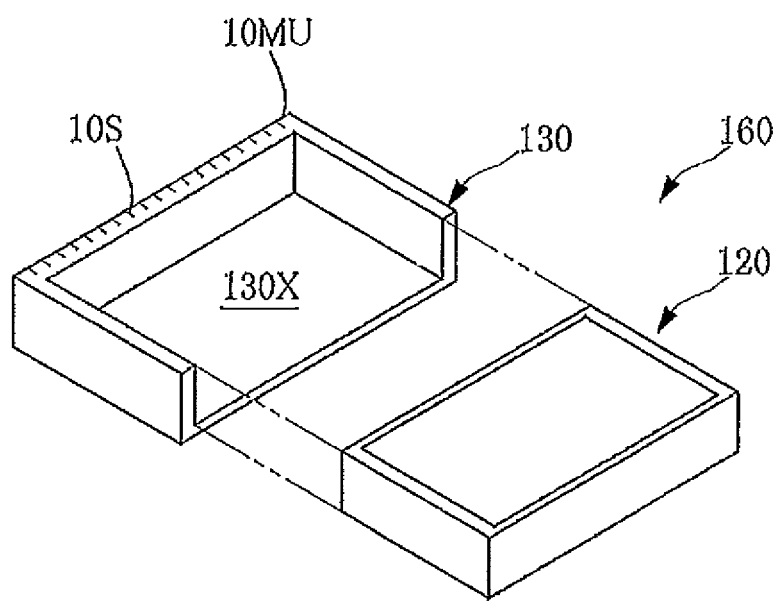
FIG. 16 is a perspective view showing an outline of the angle measuring device.

Although the angle measuring unit is contained in the case 10 and the display 20 and the operating section 40 are provided integrally with the case 10 in the angle measuring device 2 of the above-described embodiment, the present invention is not limited thereto. For example, as shown in FIG. 15, it may be an angle measuring device 140 including: a mobile terminal 120 having an angle measuring unit, a display, and an operating section; a measurement stand 130 to which or from which the mobile terminal 120 can be attached or detached; the first and second pointing mechanisms 30L and 30R; and the first and second moving mechanisms 60L and 60R. The measurement stand 130 is formed in a cuboid shape and provided at least with a mounting hole 130X into which the mobile terminal 120 is mounted. Moreover, the first and second pointing mechanisms 30L and 30R are provided on both of the side surfaces of the measurement stand 130 in the Y direction. The first and second pointing mechanisms 30L and 30R are coupled to the measurement stand 130 by the first and second moving mechanisms 60L and 60R. Needless to say, the angle measuring device may be an angle measuring device 160 including: the mobile terminal 120 having the angle measuring unit, the display, and the operating section; the measurement stand 130 to which or from which the mobile terminal 120 can be attached or detached; and the first and second pointing mechanisms 30L and 30R (see FIG. 16). In this case, the edge line 10MU of the measurement stand 130 extending in the Y direction serves as the first and second pointing mechanisms.

When it is desired to measure an angle about a measured line in order to measure a physical posture, particular sites of the skeleton are often used as first and second sites. In a case where the body shape of a measured person is of the pyknic type, however, it is difficult to find the first and second sites. Thus, a belt to be wrapped around a site of the measured person and indication seals to be attached to the belt may be used. First, the belt is wrapped around the site (for example, the torso) of the measured person. Then, after checking the positions of the first and second sites (for example, the right ASIS and the left ASIS) by means of palpation, the indication seals are attached to the belt. Then, by performing the measurement while using the indication seals attached to the belt as the first and second sites, the angle about the measured line can be measured easily.

Figure 17:
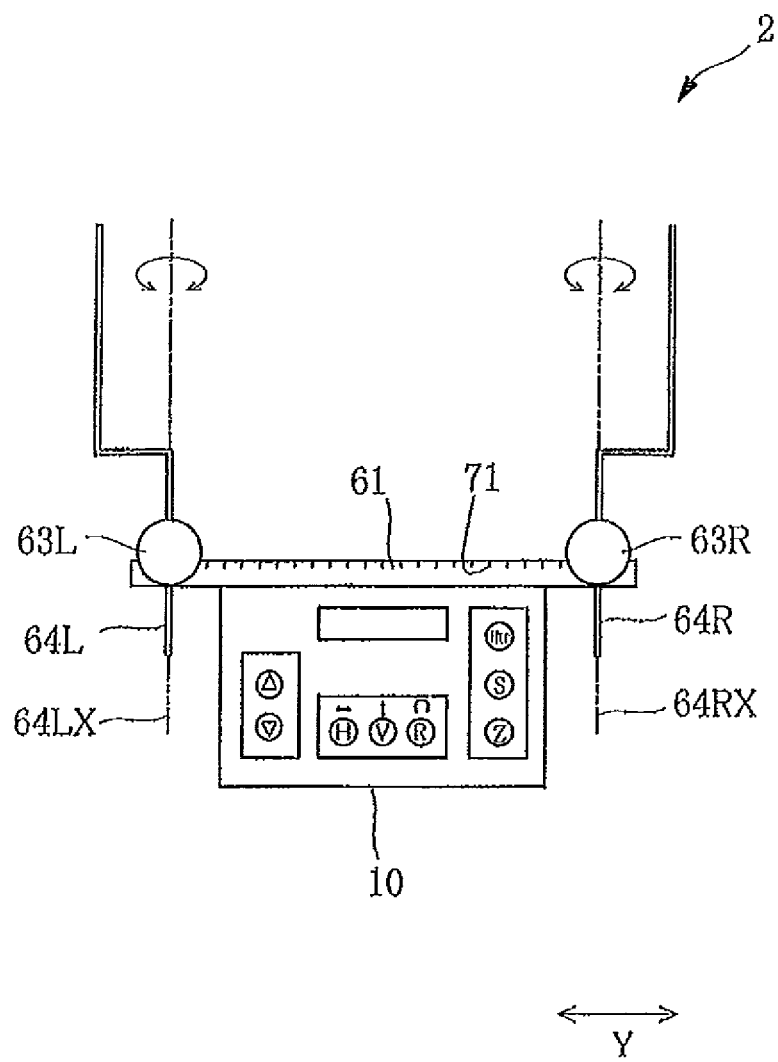
FIG. 17 is a plan view showing an outline of an angle measuring device.

Although the measuring rod 64L is linearly provided in the above-described embodiment, the present invention is not limited thereto. The measuring rod 64L may be curved (such as a wave shape or an arc shape, for example) or may be bent (such as an L-shape or a crank shape, for example). FIG. 17 shows the angle measuring device 2 having the measuring rods 64L and 64R with a crank shape. Furthermore, the crank-shaped measuring rods 64L and 64R may be turnable about axes 64LX and 64RX of portions inserted into the turning members 63L and 63R. This makes it possible to adjust the relative positions of the first and second pointing mechanisms 30L and 30R without performing the slide movement by the arms 61L and 61R. The turning mechanism that allows the measuring rod 64L to be turnable about the portion inserted into the turning member 63L may have a relative position indicator having a structure similar to that of the turning member angular scale marks 72 (see FIG. 4) and an orientation maintenance mechanism having a structure similar to that of the turning member seizing mechanism 76 (see FIG. 7A).

Although the arm main body 61LA or the like has a quadratic prism-shaped body extending long in the Y direction in the above-described embodiment, the present invention is not limited thereto. The arm main body 61LA or the like may be curved (such as a wave shape or an arc shape, for example) or may be bent (such as an L-shape or a crank shape, for example).

Although the first and second pointing mechanisms 30L and 30R and the first and second moving mechanism 60L and 60R are provided in the case 10 in the above-described embodiment, the present invention is not limited thereto. Instead of providing the first and second pointing mechanisms 30L and 30R and the first and second moving mechanisms 60L and 60R (hereinafter, collectively referred to as a measuring unit) separately from the case 10 (sensor unit), a measurement data generating section for generating measurement data and a transmitting section may be provided to the measuring unit, and a receiving section may be provided in the case 10. The measurement data generating section detects positional information about respective elements constituting the measuring unit by means of an internal sensor and generates the above-described measurement data from the detected positional information. The transmitting section then transmits the measurement data to the receiving section. As a result of such separation between the case 10 and the measuring unit, without holding the case 10 with a hand, a measurer can perform a measurement only by holding the measuring unit with a hand. Thus, the operability at the time of measurement is improved. Since this measuring unit can also measure the predetermined angle using a sensor contained in the sensor unit, it is included in angle measuring devices.

Figure 18:
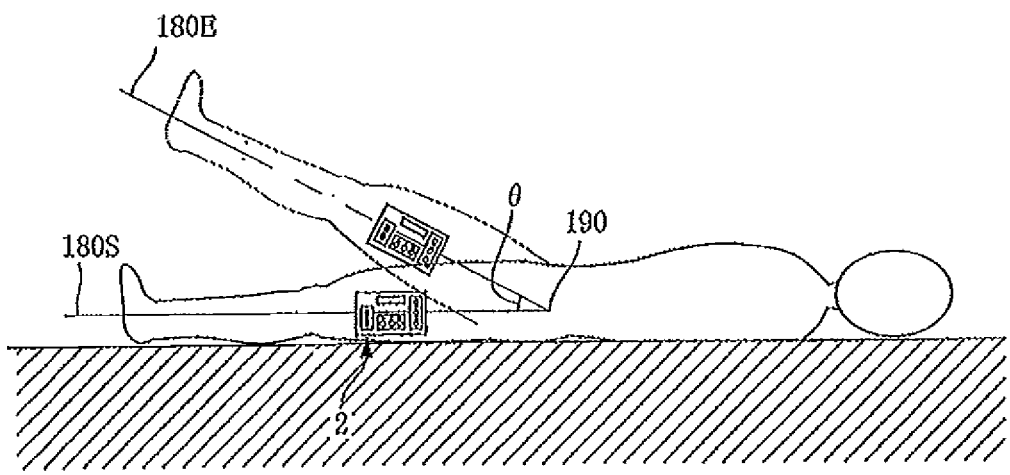

Furthermore, the above-described angle measuring device can measure a movable angle of a movable site as follows. As shown in FIG. 18, the angle measuring device 2 is fixed to a femoral region of a lying measured person (a solid line portion). Thereafter, the angle measuring device 2 sets a rotation axis for measuring a rotation angle as with the above-described rotation angle measuring mode. After the setting of the rotation axis is completed, a leg of the measured person is lifted (a two-dot chain line portion). Here, the angle measuring device 2 then performs an integral treatment on the basis of the read sensing signal to calculate the rotation angle. In this manner, the angle measuring device 2 can measure an angle between a state where the femoral region is laid (the solid line portion) and a state where the femoral region is raised (the two-dot chain line portion), i.e., an angle θ formed by a line segment 180S and a line segment 180E. The thus obtained angle θ represents the movable range of a hip joint 190. Note that a measurement about the movable range of the hip joint 190 can be performed not only on a measured person in a lying state but also on a measured person in another state (in a standing state, for example).

Figure 19:
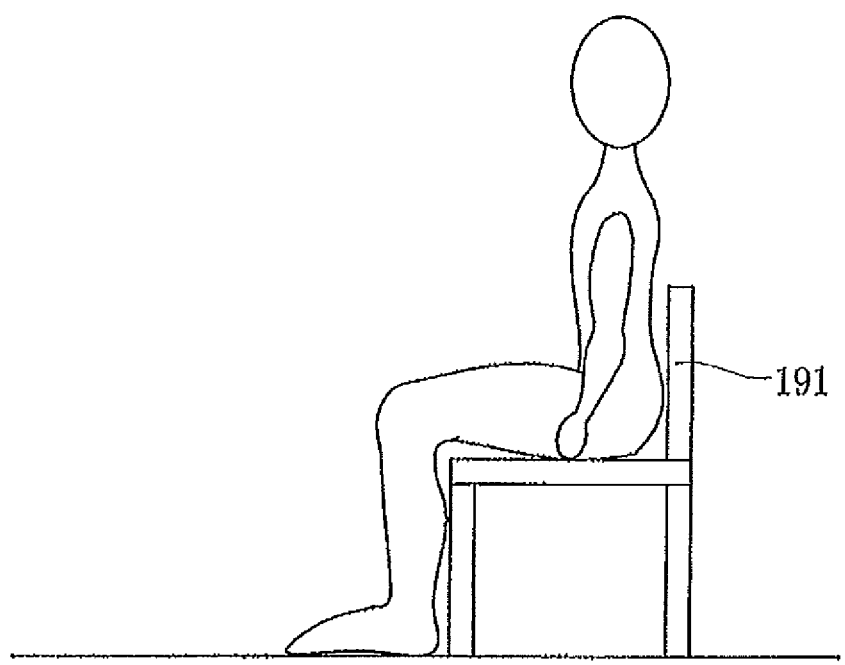
FIG. 19 is an explanatory diagram showing a posture of a person with a sufficiently wide movable range of a hip joint being seated on a chair.
Figure 20:
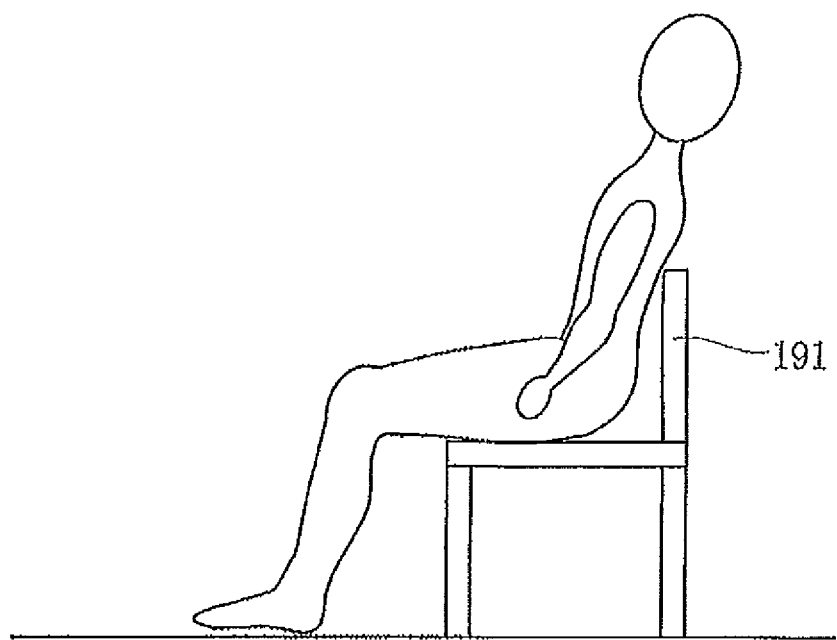
FIG. 20 is an explanatory diagram showing a posture of a person with a narrow movable range of a hip joint being seated on the chair.
Figure 21:
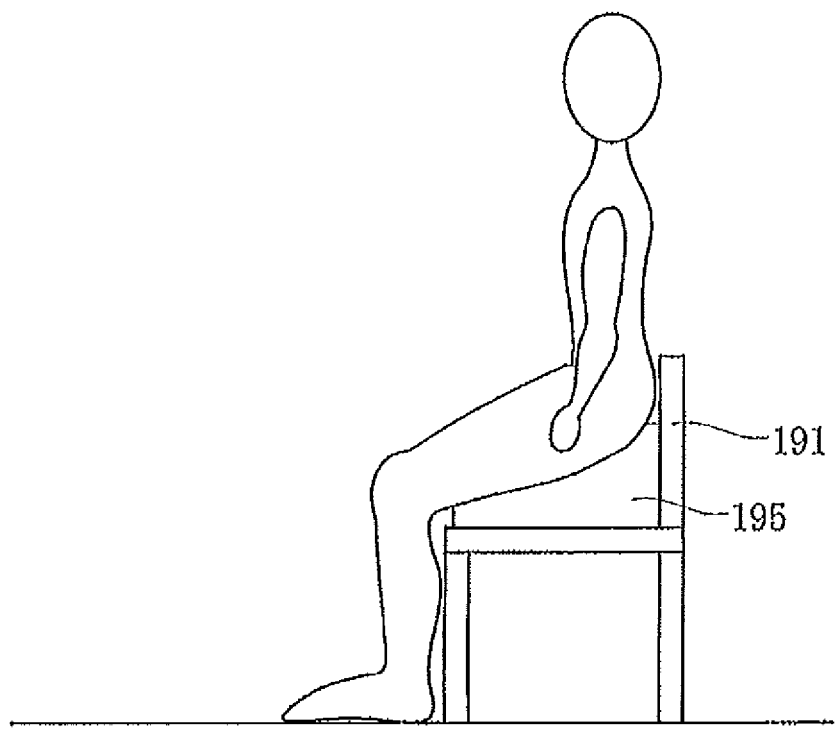
FIG. 21 is an explanatory diagram showing a posture of the person with the narrow movable range of the hip joint being seated on the chair by means of a corrective tool.

The movable range of the hip joint 190 significantly influences a seated posture on a chair 191, a wheelchair, or the like. In a case where the movable range of the hip joint 190 is sufficiently wide (90° or greater, for example) as in a non-handicapped person or the like, for example, the seated posture on the chair 191 takes a correct form (see FIG. 19). When a person with a narrow movable range of the hip joint 190 (e.g., 45°) is seated on the chair 191, on the other hand, the person cannot take a correct posture (see FIG. 20). Thus, if a person continues to take the posture as shown in FIG. 20 for a long period of time, harmful effects are imposed on the other sites. In such a case, the movable range of the hip joint for that measured person is measured and a corrective tool 195 produced on the basis of the measured movable range is used (see FIG. 21). As a result, even a person with a narrow movable range of the hip joint 190 can sit on the chair 195 with a correct posture. In the case of a wheelchair, in particular, the seated posture is maintained for a long period of time. Thus, a wheelchair user needs the corrective tool 195 adapted to the movable range of his/her hip joint. The use of the angle measuring device 2 makes it possible to measure the movable range of the hip joint 190 to be an important element when producing the corrective tool 195. Thus, the angle measuring device 2 plays an important role also when adjusting and correcting a seated posture. Although an example of the hip joint has been described as an example about the measurement for the movable range of a movable part, the present invention is not limited thereto. A measurement can be performed similarly about another movable part (shoulder, for example).

Although the movable range of the hip joint is measured only with the case 10 in the above-described embodiment, the present invention is not limited thereto. The two arms provided (the arm 61 and the arm 61LF in FIG. 12, for example) may be used. In this case, one of the arms is aligned with the line segment 180S (see FIG. 18) and the other arm is aligned with the line segment 180E (see FIG. 18). Then, the movable range of the hip joint can be measured by using the angular scale marks or the turning member seizing mechanism provided on a portion connecting the arm 61 and the arm 61LF (the end portions of the arm 61 and the arm 61LF). In a case where one arm (the arm 61L, for example) is provided in a turnable manner with respect to the case 10, one of the arm and the case 10 may be aligned with the line segment 180S and the other may be aligned with the line segment 180E.

The invention claimed is:

1. An angle measuring device for measuring an angle formed between a measured line connecting a first position and a second position on a body and a predetermined reference line by using a sensor capable of detecting the angle, the angle measuring device comprising:
   a first pointing device for pointing to the first position;
   a second pointing device for pointing to the second position;
   a first holding device for holding the first pointing device;
   a second holding device for holding the second pointing device;
   a moving mechanism that allows the first holding device and the second holding device to be movable so that a line segment connecting the first pointing device and the second pointing device and the measured line are on the same plane; and
   a relative position indicating section that indicates relative positions of the first pointing device and the second pointing device;
   the moving mechanism including a first turning mechanism and a second turning mechanism;
   the first turning mechanism allowing the first holding device and the first pointing device to be turnable about a position away from the first position;
   the second turning mechanism allowing the second holding device and the second pointing device to be turnable about a position away from the second position;
   the relative position indicating section including a first angular scale mark and a second angular scale mark;
   the first angular scale mark indicating a turned amount by the first turning mechanism associated with the first pointing device; and
   the second angular scale mark indicating a turned amount by the second turning mechanism associated with the second pointing device.

2. The angle measuring device according to claim 1, wherein:
   the first turning mechanism allows the first holding device to be turnable about a first turning axis;
   the angle measuring device includes a third turning mechanism allows the first holding device to be turnable about a second turning axis different from the first turning axis; and the angle measuring device includes a coupling mechanism couples the first turning mechanism to the third turning mechanism.

3. The angle measuring device according to claim 1, further comprising a main body having the sensor, and wherein the main body includes:
an angle informing section that informs the detected angle;
a controlling section that controls the angle informing section; and
an operating section that outputs a control signal to the controlling section.

4. An angle measuring device for measuring an angle formed between a measured line connecting a first position and a second position on a body and a predetermined reference line by using a sensor capable of detecting the angle, the angle measuring device comprising:
a first pointing device for pointing to the first position;
a second pointing device for pointing to the second position;
a first holding device for holding the first pointing device;
a second holding device for holding the second pointing device;
a moving mechanism that allows the first holding device and the second holding device to be movable so that a line segment connecting the first pointing device and the second pointing device and the measured line are on the same plane; and
a relative position indicating section that indicates relative positions of the first pointing device and the second pointing device;
the moving mechanism including a first turning mechanism and a second turning mechanism;
the first turning mechanism allowing the first holding device and the first pointing device to be turnable about a position away from the first position;
the second turning mechanism allowing the second holding device and the second pointing device to be turnable about a position away from the second position; and
the relative position indicating section being switchable between a turnable state where the first pointing device is turnable with the first holding device and a turning-regulated state where turning of the first pointing device is regulated along with turning of the first turning mechanism with the first holding device.

5. The angle measuring device according to claim 4, wherein:
the first turning mechanism allows the first holding device to be turnable about a first turning axis;
the angle measuring device includes a third turning mechanism allows the first holding device to be turnable about a second turning axis different from the first turning axis; and
the angle measuring device includes a coupling mechanism couples the first turning mechanism to the third turning mechanism.

6. The angle measuring device according to claim 4, further comprising a main body having the sensor, and wherein the main body includes:
an angle informing section that informs the detected angle;
a controlling section that controls the angle informing section; and
an operating section that outputs a control signal to the controlling section.

7. An angle measuring device for measuring an angle formed between a measured line connecting a first position and a second position on a body and a predetermined reference line by using a sensor capable of detecting the angle, the angle measuring device comprising:
a first pointing device for pointing to the first position;
a second pointing device for pointing to the second position;
a holding device for holding the first pointing device;
a moving mechanism that allows the holding device to be movable so that a line segment connecting the first pointing device and the second pointing device and the measured line are on the same plane; and
a relative position indicating section that indicates relative positions of the first pointing device and the second pointing device;
the moving mechanism including a turning mechanism that allows the holding device to be turnable about a position away from the second pointing device; and
the turning mechanism including a first turning mechanism that allows the holding device to be turnable about a first turning axis, a second turning mechanism that allows the holding device to be turnable about a second turning axis different from the first turning axis, and a coupling mechanism that couples the first turning mechanism to the second turning mechanism;
wherein the first turning mechanism allows the first pointing device to be turnable about the first turning axis, the second turning mechanism allows the first turning mechanism to be turnable about the second turning axis, and the first and turning axes cross the plane.

8. The angle measuring device according to claim 7, further comprising a main body having the sensor, and wherein the main body includes:
an angle informing section that informs the detected angle;
a controlling section that controls the angle informing section; and
an operating section that outputs a control signal to the controlling section.

9. An angle measuring device for measuring an angle formed between a measured line connecting a first position and a second position on a body and a predetermined reference line by using a sensor capable of detecting the angle, the angle measuring device comprising:
a first pointing device for pointing to the first position;
a second pointing device for pointing to the second position;
a first holding device for holding the first pointing device;
a second holding device for holding the second pointing device;
a moving mechanism that allows the first holding device and the second holding device to be movable so that a line segment connecting the first pointing device and the second pointing device and the measured line are on the same plane; and
a relative position indicating section that indicates relative positions of the first holding device and the second holding device;
the moving mechanism including:
a common arm to which the first holding device and the second holding device are attached; and
first and second moving mechanisms that allow the first holding device and the second holding device to be individually movable along the common arm;
the relative position indicating section including a relative distance scale mark provided to the common arm and indicating a relative distance between the first holding device and the second holding device;

the common arm being attached to a main body including the sensor, and a relative position of the common arm to the sensor is fixed in a state where the common arm is attached to the main body;

the moving mechanism including a first turning mechanism and a second turning mechanism;

the first turning mechanism allowing the first pointing device to be turnable with the first holding device about a position away from the first position;

the second turning mechanism allowing the second pointing device to be turnable with the second holding device about a position away from the second position; and the first turning axis of the first pointing device and the second turning axis of the second pointing device cross the plane.

10. The angle measuring device according to claim 9, wherein the main body includes:
an angle informing section that informs the detected angle;
a controlling section that controls the angle informing section; and
an operating section that outputs a control signal to the controlling section.

11. An angle measuring device for measuring an angle formed between a measured line connecting a first position and a second position on a body and a predetermined reference line by using a sensor capable of detecting the angle, the angle measuring device comprising:

a first pointing device for pointing to the first position;
a second pointing device for pointing to the second position;
a first holding device for holding the first pointing device;
a second holding device for holding the second pointing device;
a moving mechanism that allows the first holding device and the second holding device to be movable so that a line segment connecting the first pointing device and the second pointing device and the measured line are on the same plane; and
a relative position indicating section that indicates relative positions of the first holding device and the second holding device;
the moving mechanism including:
a common arm to which the first holding device and the second holding device are attached; and
first and second moving mechanisms that allow the first holding device and the second holding device to be individually movable along the common arm;
the relative position indicating section including a relative distance scale mark provided to the common arm and indicating a relative distance between the first holding device and the second holding device;
the common arm being attached to a housing device of a main body including the sensor, and a relative position of the common arm to the housing device is fixed in a state where the common arm is attached to the main body;
the moving mechanism including a first turning mechanism and a second turning mechanism;
the first turning mechanism allowing the first pointing device to be turnable with the first holding device about a position away from the first position;
the second turning mechanism allowing the second pointing device to be turnable with the second holding device about a position away from the second position; and the first turning axis of the first pointing device and the second turning axis of the second pointing device cross the plane.

12. The angle measuring device according to claim 11, wherein the first pointing device and the second pointing device, the first holding device and the second holding device, the moving mechanism, and the relative position indicating section are provided in the housing device.

13. The angle measuring device according to claim 11, wherein
the main body includes:
an angle informing section that informs the detected angle;
a controlling section that controls the angle informing section; and
an operating section that outputs a control signal to the controlling section.

14. An angle measuring device for measuring an angle formed between a measured line connecting a first position and a second position on a body and a predetermined reference line by using a sensor capable of detecting the angle, the angle measuring device comprising:

a base;
a first rod for pointing to the first position;
a second rod for pointing to the second position;
a first assembly holding the first rod and allowing the first rod to rotate relative to the base;
a second assembly holding the second rod and allowing the second rod to rotate relative to the base;
the first assembly allowing the first rod to be turnable about a position away from the first position;
the second assembly allowing the second rod to be turnable about a position away from the second position;
a first relative position indicating section including a first angular scale mark indicating a first turned amount of the first rod; and
a second relative position indicating section including a second angular scale mark indicating a second turned amount of the second rod.

15. The angle measuring device according to claim 14, wherein:
the first assembly allows the first rod to be turnable about a first turning axis;
a third assembly allows the first rod to be turnable about a second turning axis different from the first turning axis; and
a coupling mechanism couples the first assembly to the second assembly.

16. An angle measuring device for measuring an angle formed between a measured line connecting a first position and a second position on a body and a predetermined reference line by using a sensor capable of detecting the angle, the angle measuring device comprising:

a base;
a first rod for pointing to the first position;
a second rod for pointing to the second position;
a first assembly holding the first rod and allowing the first rod to rotate relative to the base;
a second assembly holding the second rod and allowing the second rod to rotate relative to the base;
a relative position indicating section that indicates relative positions of the first rod and the second rod;
the first assembly allowing the first rod to be turnable about a first turning axis;
a third assembly allowing the first rod to be turnable about a second turning axis different from the first turning axis; and a coupling mechanism that couples the first assembly to the second assembly.

* * * * *